United States Patent
Kim

[19]

[11] Patent Number: 6,159,590
[45] Date of Patent: *Dec. 12, 2000

[54] PUNCTURE AND CUT RESISTANT FABRIC

[75] Inventor: Young Hwa Kim, Woodbury, Minn.

[73] Assignee: Higher Dimension Medical, Inc., St. Paul, Minn.

[*] Notice: This patent is subject to a terminal disclaimer.

[21] Appl. No.: 08/675,146

[22] Filed: Jul. 3, 1996

[51] Int. Cl.[7] ................................................. B32B 7/08
[52] U.S. Cl. ........................... 428/223; 428/99; 428/100; 428/911; 2/2.5; 2/159; 2/160; 2/161.7
[58] Field of Search ................ 2/2.5, 159, 160, 2/161.7; 428/99, 100, 223, 911

[56] References Cited

U.S. PATENT DOCUMENTS

| | | | |
|---|---|---|---|
| 3,633,216 | 1/1972 | Schonholtz | 2/168 |
| 3,813,281 | 5/1974 | Burgess et al. | 161/159 |
| 4,442,150 | 4/1984 | Greiner et al. | 428/53 |
| 4,742,578 | 5/1988 | Seid | 2/2.5 |
| 4,833,733 | 5/1989 | Welch | 2/169 |
| 4,864,661 | 9/1989 | Gimbel | 2/167 |
| 5,070,540 | 12/1991 | Bettcher | 2/2.5 |
| 5,070,543 | 12/1991 | Beck | 2/163 |
| 5,187,815 | 2/1993 | Stern | 2/161 |
| 5,231,700 | 8/1993 | Catshall | 2/161.7 |
| 5,306,532 | 4/1994 | Tsien et al. | |
| 5,317,759 | 6/1994 | Pierce | 2/161.7 |
| 5,336,555 | 8/1994 | Darras | 428/247 |
| 5,368,930 | 11/1994 | Samples | 428/323 |
| 5,407,612 | 4/1995 | Gould | 264/24 |
| 5,423,090 | 6/1995 | Gimbel | 2/161.7 |
| 5,428,841 | 7/1995 | Stein | 2/168 |
| 5,442,815 | 8/1995 | Cordova | 2/161.7 |
| 5,442,816 | 8/1995 | Sekets | 2/161.7 |
| 5,601,895 | 2/1997 | Cunningham | 428/66.6 |

FOREIGN PATENT DOCUMENTS

| | | | |
|---|---|---|---|
| 0 657 110 A1 | 6/1995 | European Pat. Off. | F41D 13/10 |
| 2 287 639 | 9/1995 | United Kingdom | F41H 1/02 |
| 2 302 794 | 2/1997 | United Kingdom | F41H 1/02 |
| WO 92/08094 | 5/1992 | WIPO | F41H 1/02 |
| WO93/21492 | 10/1993 | WIPO | F41H 1/02 |
| WO 95/07033 | 3/1995 | WIPO . | |

*Primary Examiner*—Terrel Morris
*Assistant Examiner*—Ula C. Ruddock
*Attorney, Agent, or Firm*—Gray, Plant, Mooty, Mooty & Bennett, P.A.

[57] ABSTRACT

A puncture and cut resistant fabric comprised of identical platelets and rivets arranged into an array whereby the tops of adjacent platelets are reversed so that tabs on each platelet slidably engage with tabs of each adjacent platelet and are held in engagement by hooks depending from each tab and the rivets placed through apertures formed by the edges of the tabs. The fabric is twistable, bendable, and stretchable. It is constructed of material that will withstand cutting and piercing forces encountered in medical or other environments and is of thin walled construction to allow ease of use.

53 Claims, 22 Drawing Sheets

Fig. 13B
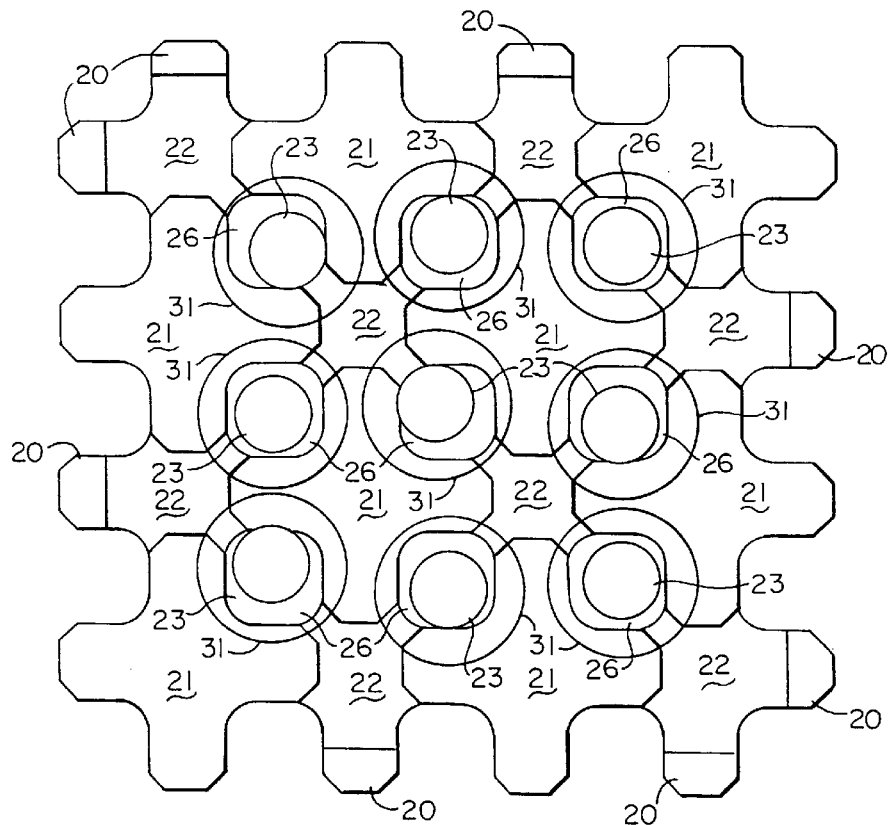
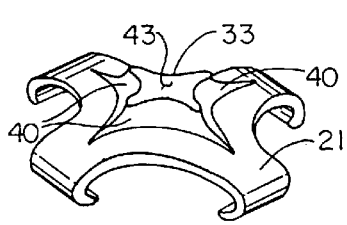
Fig. 14A
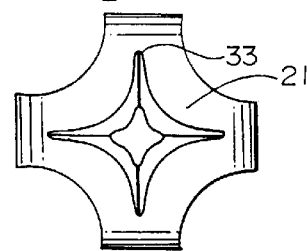
Fig. 14B
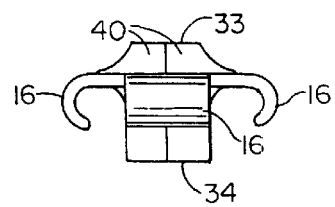
Fig. 14C
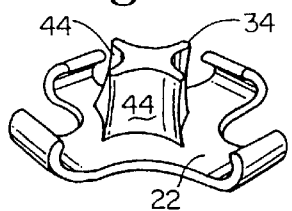
Fig. 14D
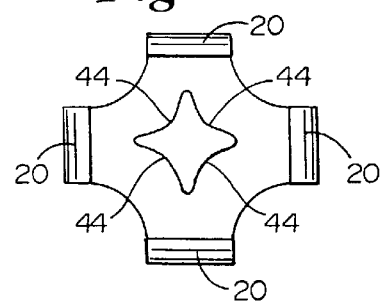
Fig. 14E
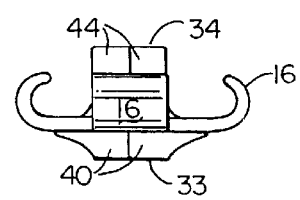
Fig. 14F

PUNCTURE AND CUT RESISTANT FABRIC

FIELD OF THE INVENTION

This invention relates generally to a puncture and cut resistant fabric. More particularly, this invention relates to a fabric consisting of an array of loosely interconnected platelets forming a flexible web suitable for use in surgical gloves and other garments worn in an operating environment where sharp instruments are prevalent. This invention further relates to a method of making protective garments incorporating the puncture and cut resistant fabric.

BACKGROUND OF THE INVENTION

With the prevalence of AIDS it has become increasingly clear that there is a strong need for materials that will resist puncture and cuts during medical procedures, which generally expose medical personnel to sharp objects such as scalpels and needles for suturing and for injecting fluids. Although, AIDS has been the primary force behind the search for protection from blood borne infections, there is a host of such infections. Hepatitis and the Ebola infections are just two more examples of serious life threatening blood borne infections.

Surgical gloves are fabricated of an elastomeric polymeric material to act as a barrier to fluid flow and bacterial transmission between the patient and the care giver. They are most generally made from a thin layer of latex. Latex gloves allow the surgeon to retain a very high level of tactile sensitivity and ease of finger manipulation, but are easily cut by a scalpel or punctured by a needle.

There have been numerous attempts to fabricate a surgical glove that is cut and puncture resistant and yet retains characteristics necessary to perform delicate surgical procedures. In particular, such a glove must allow the wearer to feel the surface on which he or she is working. In other words, it must preserve tactile sensitivity. The glove must also be stretchable, bendable, and twistable. The universally used latex glove has all of these properties, except the property of cut and puncture resistance.

Various approaches have been tried to provide the surgical glove with today's additional requirement of cut and puncture resistance. For example, U.S. Pat. No. 4,742,578, to Seid, issued May 10, 1988 reinforces a surgical glove with an overlay of thin pliable material composed of a large number of tightly interlaced fibers or filaments of high strength. While this reportedly provides increased resistance to penetration, the margin of safety is far too low when faced with blood borne infections. U.S. Pat. No. 4,833,733, to Welch, issued May 30, 1989 incorporates a web of interwoven synthetic fibers such as nylon and aramid to provide some level of cut resistance, but due to the inherent porosity of the weave, it offers no puncture resistance. U.S. Pat. No. 4,864,661, to Gimbel, issued Sep. 12, 1989 purports to offer puncture resistance, but not cut resistance. Gimbel uses a woven fabric placed at high risk areas of the glove such as portions of the fingers. A woven fabric presents the possibility that a needle will be able to penetrate the fabric through the interstices formed by the intersecting fibers. U.S. Pat. No. 5,070,540, to Bettcher, issued Dec. 10, 1991 provides cut resistance using bundles of wire and fiber strands. The strands are situated throughout the entire glove. Bettcher does not purport to provide puncture resistance. The wire and fiber strands limit flexibility of the glove, a major requirement of a surgeon. U.S. Pat. No. 5,317,759, to Pierce, issued Jun. 7, 1994 is a glove with pillars extending perpendicular to the plane of the glove between outer and interior glove layers of a latex type material. The pillars reduce the chance of a suture needle piercing the glove, since, as the suture angles through the glove, it will most likely contact a pillar. This glove design suffers from the inability to stop a hypodermic needle piercing the glove at an angle close to perpendicular to the plane of the glove material. It also is not cut resistant and the rigid embedded pillars substantially reduce flexibility of the glove. U.S. Pat. No. 5,368,930, to Samples, issued Nov. 29, 1994 is an elastomeric sheet material with enhanced puncture resistance. Imbedded in the material are plate-like non-elastomeric particles. This material suffers from at least two deficiencies. It is not cut proof and the embedded plates make the material very stiff. U.S. Pat. No. 5,407,612, to Gould, issued Apr. 18, 1995 is similar to the Samples material. It has flat plates oriented parallel to the elastomeric glove material and embedded in the glove material. This has the unfortunate effect of acting like reinforcing rods in cement. The glove as a result becomes inflexible. While there have been other attempts to make a cut proof or a puncture proof surgical glove, they also fail to meet the unique combination of characteristics required by the surgical process.

As pointed out in this section by the review of certain patented gloves and glove material, there have been attempts to solve the major need of an effective and reliable barrier material to body fluid transmission between the health professional and the patient. Yet, this need must be met while maintaining the health professional's ability to carry on his or her task of surgery, drawing bodily fluids, or other such activity. Each of the currently available gloves or barrier material lacks one or more of the necessary properties for an effective surgical barrier. The properties include: (1) cut resistance, (2) puncture resistance, (3) flexibility, (4) bendability, (5) twistability, (5) stretchability, (6) ability to maintain the user's tactile sensitivity, and (7) an effective barrier to transmission of body fluids.

The object of this invention is to provide an effective cut and puncture resistant barrier, for use in conjunction with conventional fluid barrier materials, that has all of the necessary properties for use in the medical and other fields where the transmission of body fluids between the care-giver and the patient must be eliminated.

SUMMARY OF THE INVENTION

According to the present invention, the foregoing object and other objects and advantages are attained by provision of a fabric of a cut and puncture resistant material. The fabric retains the necessary properties of flexibility, including bendability, stretchability, and twistability by an array of loosely coupled small platelets hooked together by integral tabs depending from the platelet to form a two dimensional sheet of fabric. Each platelet has tabs extending from each of its edges. The tabs of adjacent platelets loosely interconnect. The base of each platelet is a very thin wafer having a thickness much less than either its outer dimensions. The platelets are constructed of a hard and strong material that is not brittle. A typical density of platelets is 100 per square centimeter of fabric.

In accordance with another aspect of the invention, a plurality of rivets are inserted into an aperture, which is formed by the interconnected tabs of adjacent platelets. The rivets are inserted at a right angle to the plane of the fabric. The rivets completely cover the void surrounded by the interconnected tabs so that a virtually solid fabric is created, which blocks the path of a puncturing object such as a hypodermic needle or suture.

The tab extends from the edge of the platelet in the same plane as the base of the platelet. At the end of the tab distal from the base of the platelet, the tab terminates in a hook extending away from the plane of the base of the platelet.

In one embodiment of the invention, the width of the tab is less than the length of the edge of the base of the platelet.

Another aspect of the invention is a platelet with four equal sides, although other equal sided polygons will also result in a suitable fabric.

To provide a fabric suitable for manufacturability, all of the platelets are identical. The fabric is assembled by connecting the tabs of each platelet to the tab of adjacent platelets, which adjacent platelets have the plane of its base rotated 180 degrees about an axis parallel to and through the plane of the adjacent platelet. Thus every platelet in the array of platelets that make up the fabric has the hooks of its tabs reversed from those of its adjacent platelets. That is, the top of each adjacent platelet is flipped over so that the top is facing down instead of up. The fabric created is an array having platelets with tops up alternating with platelets with tops down in both rows and columns.

The fabric of the invention, comprising a two dimensional sheet of platelets having tabs on each edge of the base of the platelet for loose interconnection of the platelets, when combined between two elastomeric layers forms a cut and puncture resistant material suitable for fabrication of surgical gloves and other wearing apparel for use in an operating room and for other purposes where a barrier to transmission of bodily fluids is required, and the risk of puncture or cuts is high.

Still other objects and advantages of the present invention will become readily apparent to those skilled in this art from the following detailed description. To illustrate the invention, the detailed description shows and describes only the preferred embodiments of the invention. However, as will be realized, the invention is capable of modification in various obvious respects, without departing from the invention. Accordingly, the drawings and detailed description are to be regarded as illustrative in nature, and not as restrictive.

BRIEF DESCRIPTION OF THE DRAWINGS

FIG. 13B is a plan view of the fabric with rivets at different locations in the aperture with heads that cover the aperture in each case.

FIGS. 14A through F depicts a platelet with a head and plug of an alternate embodiment in perspective, plan, and side views.

DETAILED DESCRIPTION OF THE PREFERRED EMBODIMENTS

The following description of a cut and puncture resistant fabric for medical apparel is provided to enable any person skilled in the art to make and use the invention and sets forth the best modes contemplated by the inventor for carrying out the invention. Various modifications, however, will remain readily apparent to those skilled in the art, since the generic principles of the present invention have been defined herein.

Figure 1B:
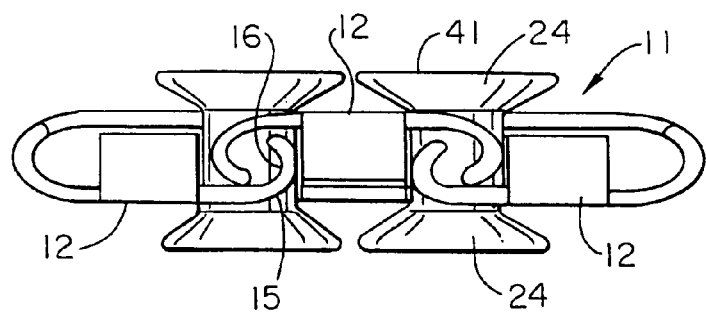
FIG. 1B is a cut-away side view along line A—A of FIG. 1A.
Figure 1A:
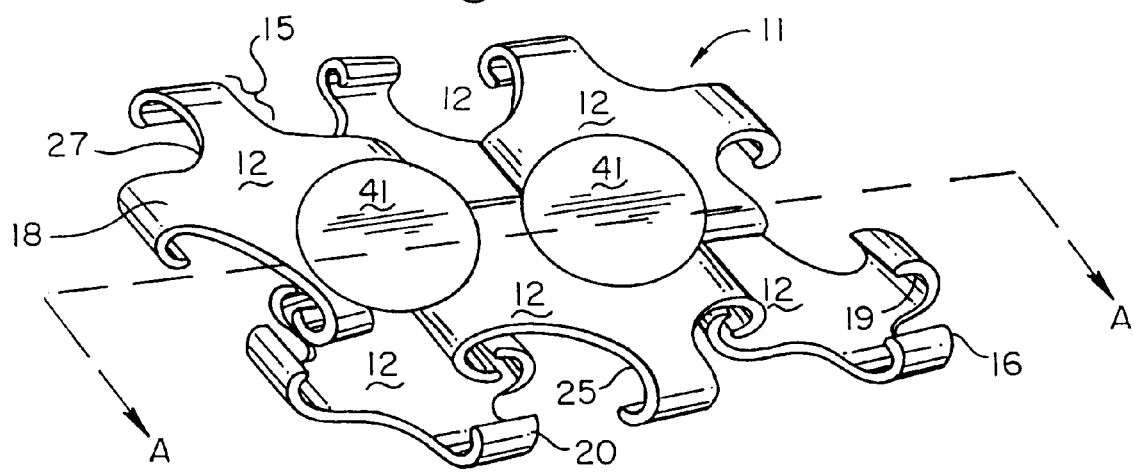
FIG. 1A is a perspective view of the fabric of the invention.
Figure 1C:
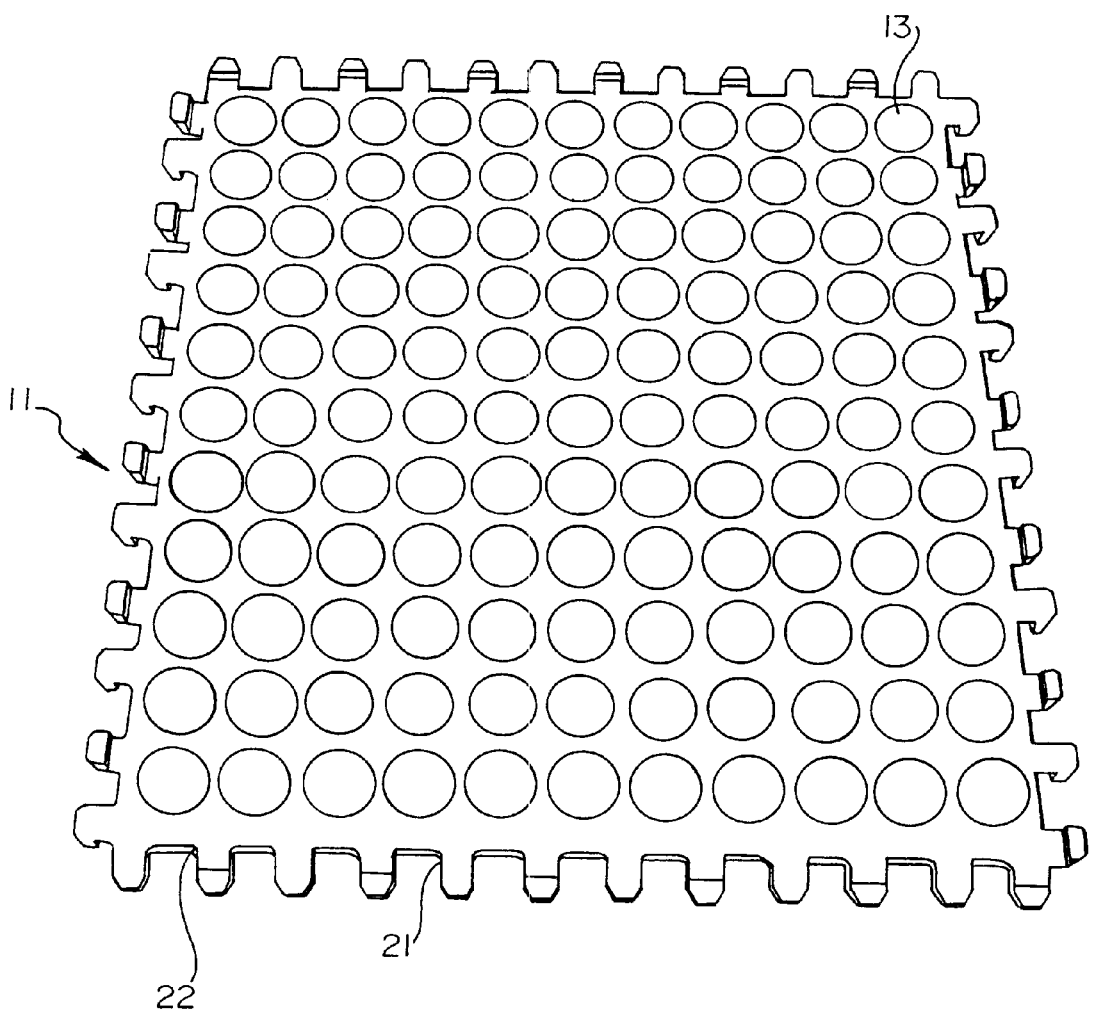
FIG. 1C depicts a large array of fabric
Figure 8A:
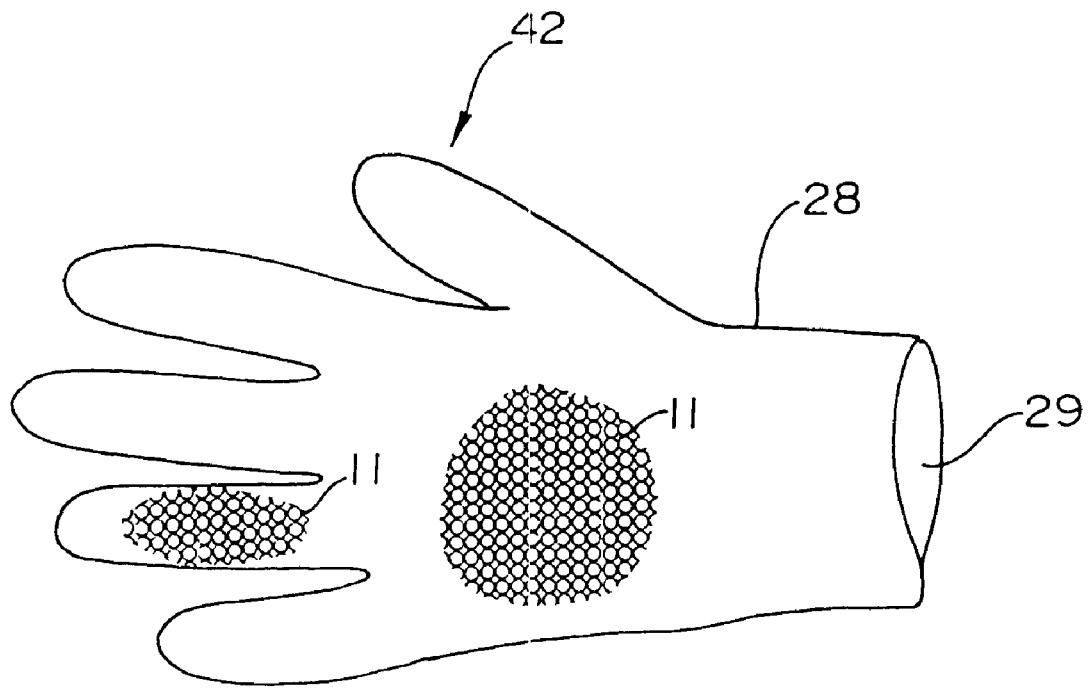
FIG. 8A is a perspective view of a surgical glove fabricated using the fabric with sections of the top layer of material cut-away to show the fabric.
Figure 8B:
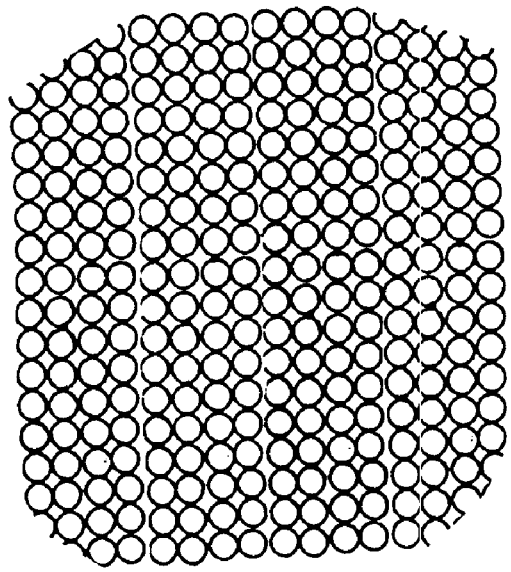
FIG. 8B is an enlargement of the detail shown in the cut-away of FIG. 8B.

FIG. 1A depicts a perspective view of an embodiment of the fabric 11 of the present invention. FIG. 1B is a cut-away side view along line A—A of FIG. 1A. FIG. 1C depicts a large array of the fabric 11 comprised of platelets 12, alternately with their bottoms 22 up and their tops 21 up, and rivets 13. The fabric 11 is constructed of very thin rigid platelets 12 and rivets 13, which are chosen to resist a puncture force equivalent to that exerted by a hypodermic needle in a medical environment. As can be seen from FIGS. 1A, B, and C and the other figures illustrating the invention in this specification, there is no area of the fabric 11 that is not covered by either a rivet 13 or a platelet 12, thereby, foreclosing the penetration of a needle striking the fabric 11. Specifying a material that will resist a needle puncture also results in a material that will resist cuts from instruments encountered in a medical setting, such as scalpels. The fabric 11 of the invention is intended to be sandwiched between an upper and lower layer 28 and 29 of material that acts as a barrier to transmission of bodily fluids, as shown by the surgical glove in FIG. 8. An example of such a material is an elastomeric polymer such as latex. It is not necessary that the upper layer 28 be a fluid barrier, although it is preferable. Typically, latex for gloves is approximately 0.2 millimeters thick, which is thick enough to cover the fabric 11 with an upper or lower layer 28 or 29. The fabric 11 is sandwiched between the upper and lower layers 28 and 29 with minimal or no attachments to those layers to allow the fabric free movement in all directions. To further promote free movement of the fabric 11 independent of the upper and lower layers 28 and 29, the surfaces of the fabric 11 and the sides of the upper and lower layers 28 and 29 in contact with the fabric 11 are lubricated with, for example, silicone. The silicone serves two functions. It assists the fabric 11 to freely bend, stretch, and twist and it decouples the fabric from the upper and lower layers 28 and 29 by imparting the fabric 11 with an anti-adhering property. While attachment of the fabric 11 to the upper and lower layers 28 and 29 must be kept at a minimum, attachment around the cuff, at the ends of the fingers, at one point on the back of the hand, and at one point on the palm prevents slippage of the fabric 11 relative to the upper and lower layers 28 and 29. The fabric is a useful component in other medical wearing apparel such as sleeves and aprons. It also has application for protective garments for those working in occupations such as a machinist or butcher. Garments for these other occupations as well as for differing applications in the medical field will require differing material type and thickness and dimensions of the platelets 12 and rivets 13, since the forces which come to bear upon the material will vary. Even in the case of surgical gloves 42, the material sizes and type may vary, since surgery and routine drawing of blood, for example, are performed under different conditions. It may not be necessary to fortify the entire glove 42 with the fabric 11. The fabric 11 may be placed strategically at only high risk zones. The size of a stainless steel platelet 12 for a medical glove 42 application would be approximately one square millimeter. The diameter of the rivet 13 would be approximately 0.2 millimeters.

The rigid material for manufacturing the platelets 12 and rivets 13 is currently available as off-the-shelf goods. The material can be metal, such as stainless steel, titanium, or metal alloys, ceramic, plastic, such as Teflon, or any other material that resists the specified puncture and cutting forces at a thickness of approximately one millimeter. Any material should preferably not be brittle.

The process of assembling the rivets 13 and platelets 12 into the fabric 11 is performed by currently available production technology.

Figure 2A:
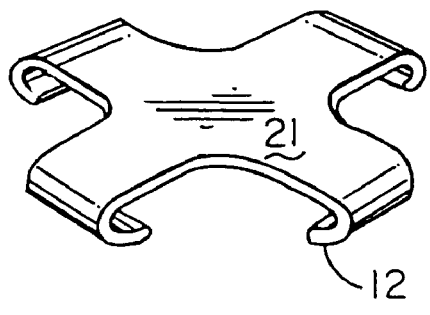
FIG. 2A is a perspective view of the top of the platelet.
Figure 2B:
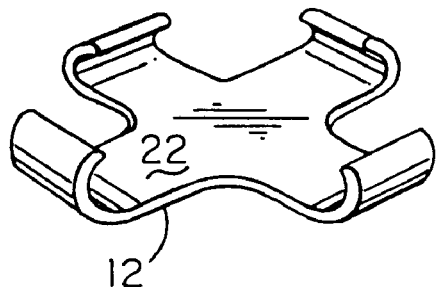
FIG. 2B is a perspective view of the bottom of the platelet.
Figure 2C:
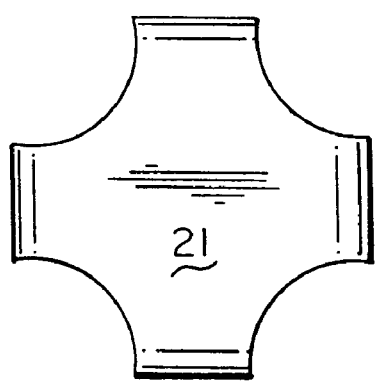
FIG. 2C is a plan view of the top of a platelet.
Figure 2D:
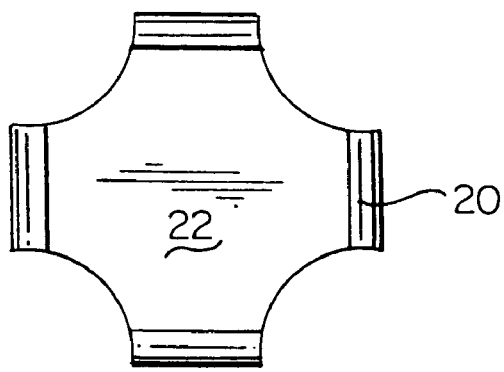
FIG. 2D is a plan view of the bottom of a platelet.
Figure 2E:
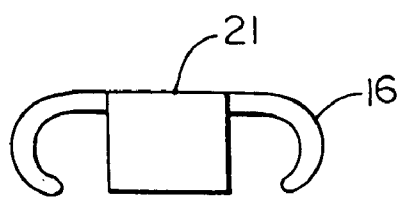
FIG. 2E is an elevation view of a platelet with the hooks down.
Figure 2F:
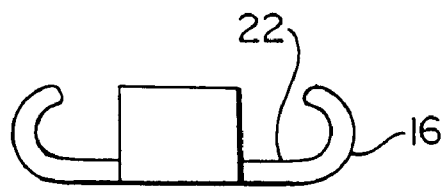
FIG. 2F is an elevation view of a platelet with the hooks up.

FIGS. 2A through 2F are various views and orientations of an embodiment of a platelet 12, the basic building block of the fabric 11. FIG. 2A is a top perspective view of the platelet 12. FIG. 2B is a bottom perspective view. FIG. 2C is a top plan view and FIG. 2D is a bottom plan view. FIGS. 2E and 2F are side views of the platelet 12, respectively.

Figure 3A:
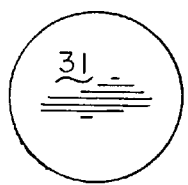
FIG. 3A is a plan view of one embodiment of a rivet.
Figure 3B:
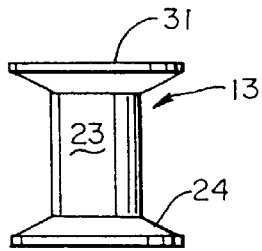
FIG. 3B is an elevation view of the rivet of FIG. 3A.
Figure 3C:
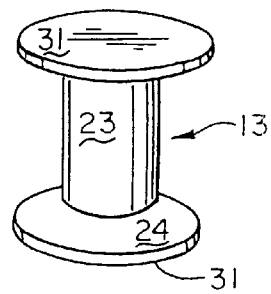
FIG. 3C is a perspective of the rivet of FIG. 3A.
Figure 3D:
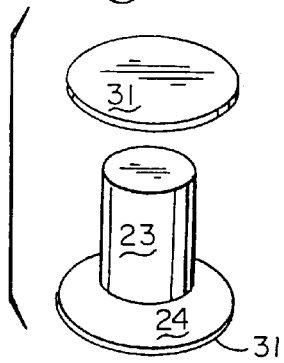
FIG. 3D is a perspective view of the rivet of FIG. 3A with one of the truncated cones separated.
Figure 3E:
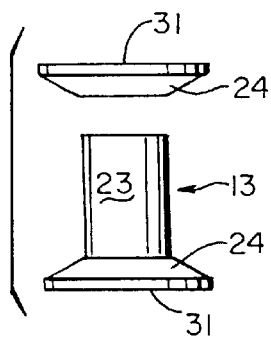
FIG. 3E is an elevational view of the rivet with one of the truncated cones separated.
Figure 3F:
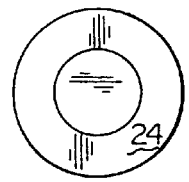
FIG. 3F is a plan view of the separated truncated cone shown in FIG. 3D from the truncated cone end.

FIGS. 3A through 3D are views of an embodiment of a rivet 13, the only other building block of the fabric 11. FIG. 3A is a top view of the rivet 13, which consists of a pin 23 and two truncated cone heads 24 at each end of the pin 23. FIG. 3F shows where the top of the pin 23 of the rivet 13 is connected as a circle concentric with the top of the truncated cone head 24. One method of assembling fabric 11 employs a rivet 13 with one of the truncated cone heads 24 separated from the rivet 13, as shown in FIG. 3D. A pin 23 with one of the truncated cone heads 24 remaining attached is inserted through the aperture 26, shown in FIGS. 7A and 7B, until further movement is stopped by the attached truncated cone head 24 and the separated truncated cone head 24 is fused onto the other end of the pin 23 by a welding or some other process.

Figure 4A:
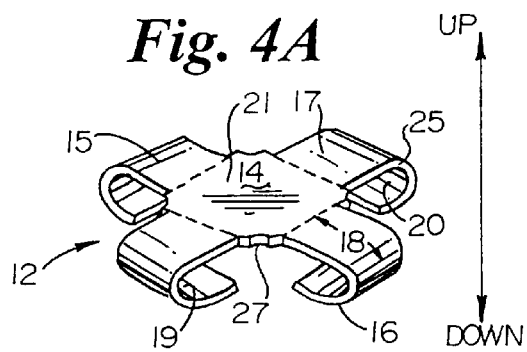
FIG. 4A is an enlarged perspective of the top of a platelet.
Figure 4B:
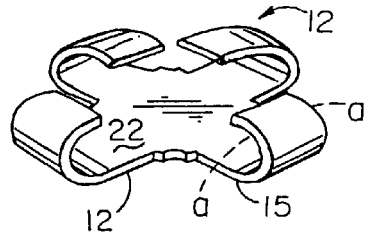
FIG. 4B is an enlarged perspective view of the bottom of a platelet.

FIGS. 4A and 4B, enlarged views of one embodiment of a platelet 12, illustrate the nomenclature used to identify the various portions of the platelet 12. The figures also arbitrarily establish the up and down direction for purposes of discussion in this specification. FIG. 4A is a view of the top 21 and FIG. 4B is a view of the bottom 22 of platelet 12. The area within the dotted lines is referred to as the base 14 of the platelet 12. The base 14 is a planar surface. The portions of the platelet 12 depending from a platelet base edge 17 is the tab 15. The tab 15 portion is more clearly indicated in FIG. 4B by the portion of FIG. 4B lying towards the right of line a—a. In the embodiment shown in FIGS. 4A and B, the tab terminates at the end distal to the base 17 in arc 19, which extends away from, and perpendicular to, the plane of the base 14 of the platelet 12. The arc 19 of the tab 15 is aligned with the arm 18 portion of the tab 15 as shown in FIG. 2A through 2F. The hook 16 of the platelet 12 is formed by the arc 19 and reverse tab portion 20. The reverse tab portion 20 is the portion of the hook 16 that reverses back towards the base edge 17 of the platelet 12. The arm 18 of the tab 15 is a planar surface and is in the same plane as the base 14 of the platelet 12. The width of the tab 15 is less than the length of the base edge 17 of the platelet 12. In the preferred embodiment, the base 14 of the platelet 12 is a polygon having four equal sides.

Figure 5:
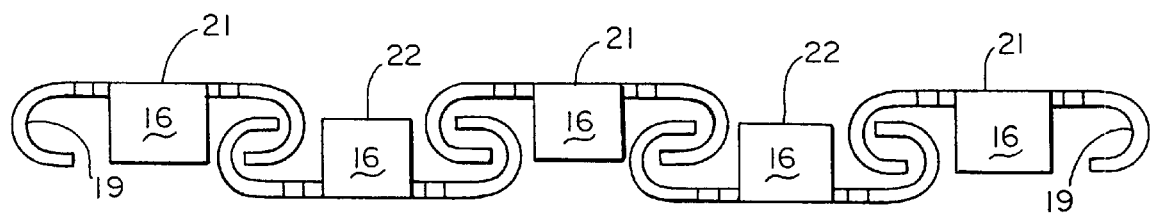
FIG. 5 is a cut-away view of a one dimensional chain of loosely interconnected platelets.

A continuous two dimensional sheet of fabric 11 of any length or width is assembled by interconnecting multiple platelets 12 and rivets 13 in an array as shown in FIGS. 1A and 1B and 6A through 6C. Each of the platelets 12 and rivets 13 that make up the fabric are identical. The orientation of adjacent platelets 12 are reversed so that the hooks 16 of each platelet 12 are interconnected as shown in FIG. 5. FIG. 5 shows a one dimensional string of platelets 12 viewed in cut-away from the side. In the actual fabric 11 as shown in FIGS. 1A, 1B, and 6A through 6C, the tabs 15 of each adjacent platelet 12 are interconnected on four sides by mating the opposing hooks 16 of the adjacent platelets 12 having their bottoms 22 up with those of the platelets 12 having their tops 21 up. The orientation of the adjacent platelets 12 differs only in that adjacent platelet 12 is rotated so that the bottom 22 of the adjacent platelet 12 faces upward as illustrated in FIGS. 1, 5, and 6.

Figure 6A:
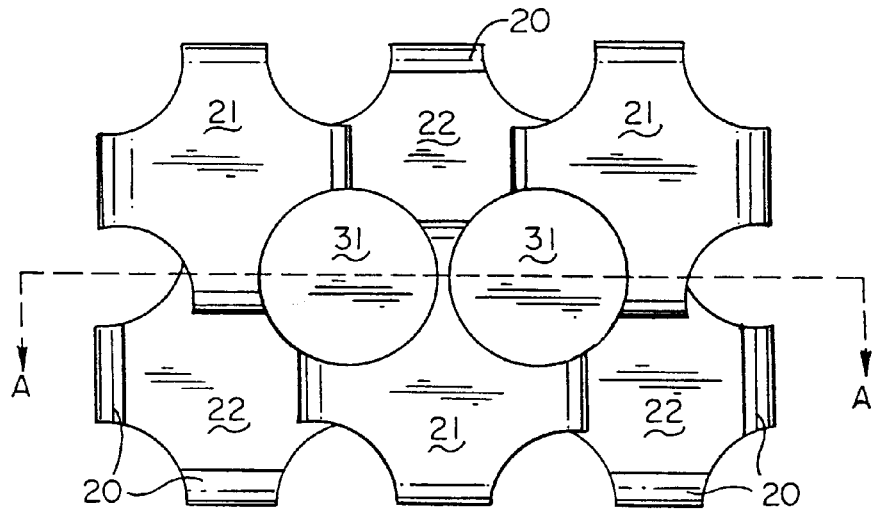
FIG. 6A is a plan view of the fabric, wherein dotted line A—A represents an imaginary plane that cuts the fabric into two pieces.
Figure 6B:
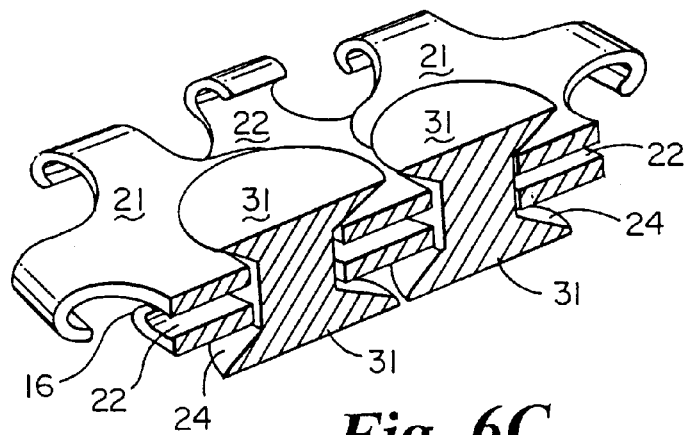
FIG. 6B is a perspective view of a segment of the fabric of the invention cut through the fabric by a plane normal to the fabric along line A—A of FIG. 6A.
Figure 6C:
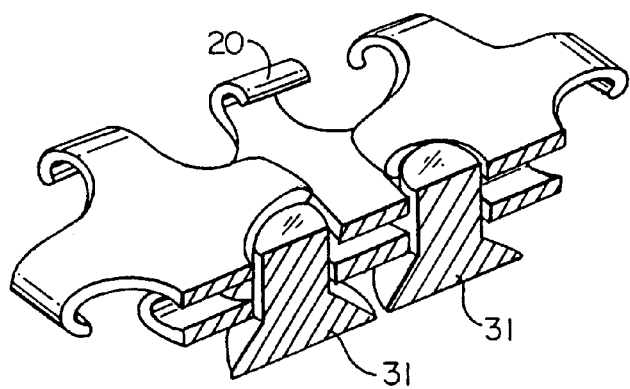
FIG. 6C is another perspective view of a segment of the fabric cut through the fabric by a plane normal to the fabric along a line A—A of FIG. 6A with the truncated cone of one side of the rivets cut off.
Figure 7A:
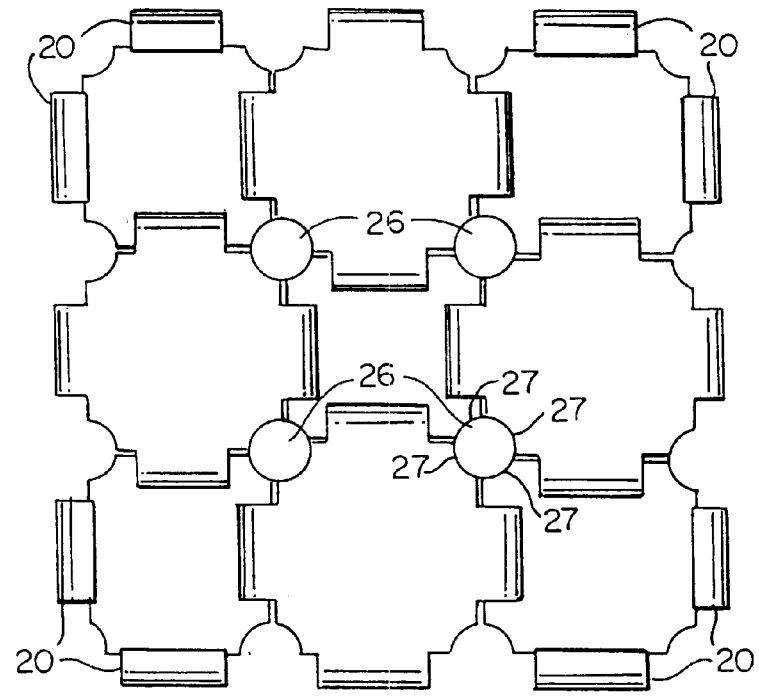
FIG. 7A is a plan view of the fabric, without rivets, with the platelets in a fully compressed configuration with minimum surface area.
Figure 7B:
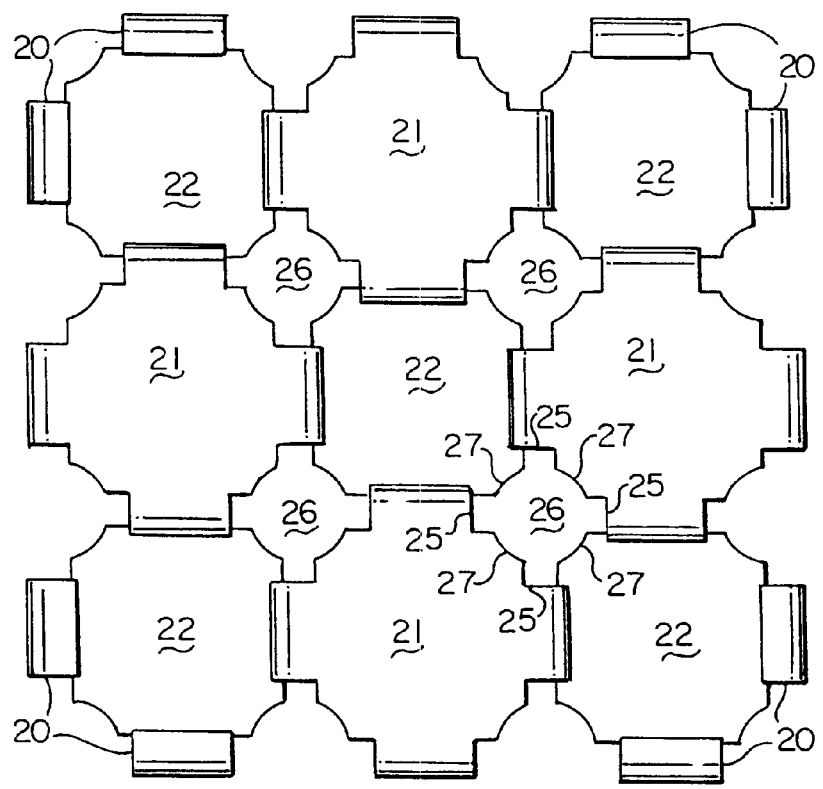
FIG. 7B is a plan view of the fabric, without rivets, with the platelets in a fully stretched configuration with the maximum surface area.

The pins 23 of rivets 13 are inserted perpendicular to the plane of the fabric 11 through the apertures 26, shown in FIGS. 7A and 7B, formed by the tab edges 25 and the concave arc 27 that forms the intersection of adjacent base edges 17 of the platelet 12 and the tab edges 25 and the concave arc 27 of adjacent interconnected platelets 12. The rivets 13 are locked into the fabric 11 perpendicular to its plane by the truncated cone 24 ends as shown in FIGS. 6A, 6B, and 6C. The pin 23 is of a length that allows a slight movement of the rivet perpendicular to the fabric. The diameter of the pin 23 is almost the same as the diameter of the aperture 26 when the fabric 11 is fully compressed as shown in FIG. 7A to form what is commonly referred to as a push fit between the pin 23 and the aperture 26. The push fit of the rivet 13, even when the fabric 11 is in its fully compressed state, allows for flexibility of the fabric 11 as well as transmission of tactile forces through the fabric 11 so that the wearer retains an ability to feel or sense surgical procedures.

To allow for flexibility, which includes the properties of stretchability, bendability, and twistability, the hooks 16 must be dimensioned appropriately relative to adjacent hooks 16. The rivets 13 must also be dimensioned appropriately relative to the aperture 26 in which it is inserted. Although, the meaning of the terms stretchability, bendability, and twistability is generally appreciated, reference to FIGS. 9, 10, 11, and 12 are helpful to understand the unique means by which this fabric 11 is able to achieve these requirements and the importance of the dimensions of the hooks and the rivets in relation to the aperture.

Figure 9C:
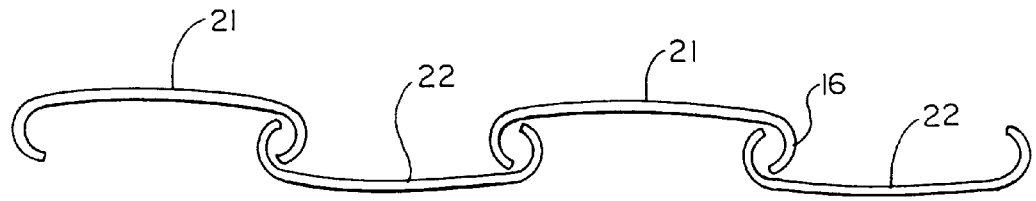
FIG. 9C is a cross section of the line of platelets of FIG. 9A.
Figure 9D:
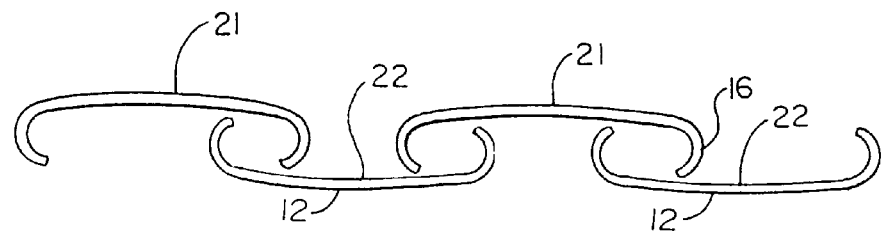
FIG. 9D is a cross section of the line of platelets of FIG. 9B.
Figure 9A:
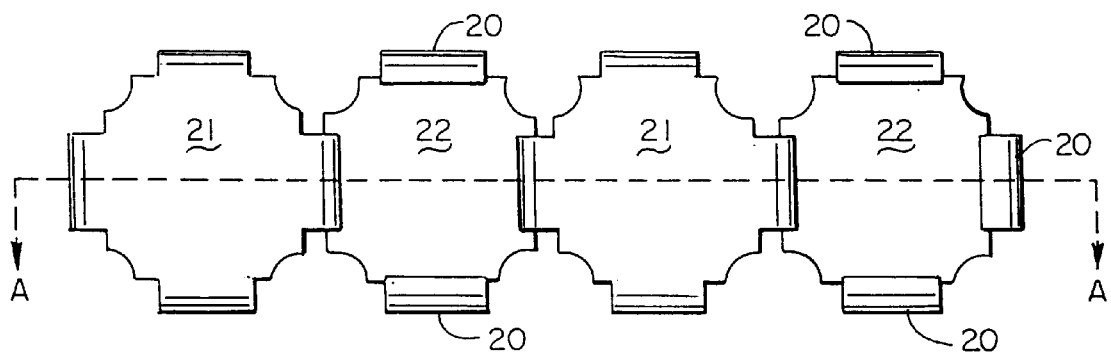
FIG. 9A is a plan view of a line of platelets fully stretched.
Figure 9B:
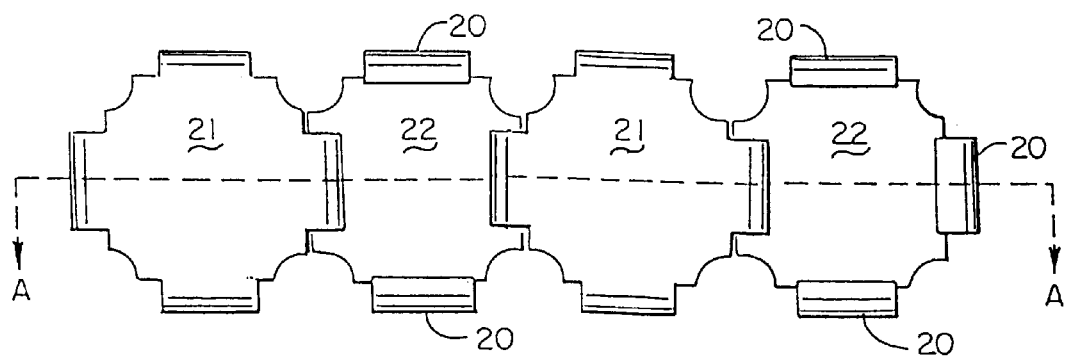
FIG. 9B is a plan view of a line of platelets fully compressed.

FIG. 9A illustrates a line of platelets 12 connected in accordance with the invention. FIG. 9A shows the platelets 12 in a configuration of maximum separation. FIG. 9B illustrates the platelets in a configuration of minimum separation. FIG. 9C is a cross-section taken along line a—a of FIG. 9A. FIG. 9C illustrates how the hooks 16 can be pulled to their outer extremities and yet not separate due to the positive engagement of the hooks 16. The hook 16 of each platelet 12 slides along the bottom of its matingly engaged platelet 12 until the maximum stretch, or length, of the string of platelets 12 is achieved. FIG. 9D is a cross-section taken along line a—a of FIG. 9B. FIG. 9D illustrates how the hooks 16 can slide towards the center of each platelet 12 to arrive at the point of least stretch, or length.

Figure 10A:
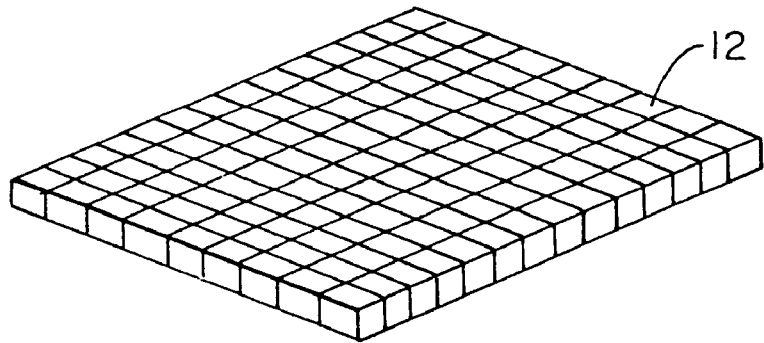
FIGS. 10A and B illustrate bendability of the fabric of the invention.
Figure 10B:
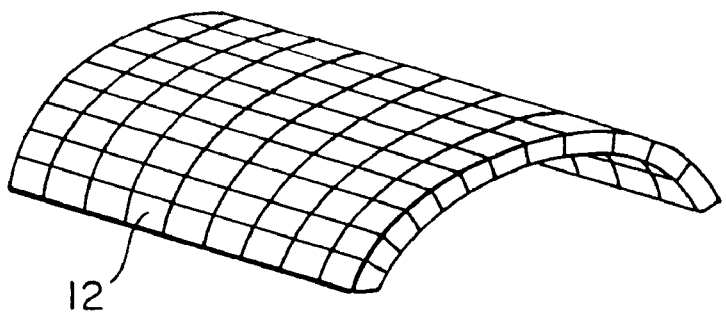

Bendability of the fabric 11 is illustrated in FIGS. 10A and B where each block denotes one platelet 12. FIG. 10A shows the fabric 11 as a flat array of platelets. FIG. 10B shows the fabric 11 bent in a curve. The property of bendability is the result of the hooks 16 allowing for arcuate movement of one platelet 12 relative to another. The arc 19 of the hook 16 facilitates this radial movement, but a planar hook 38 with a finger 30, as shown in FIG. 24 projecting downward from the distal end of the arm 18 of the tab 15 also allows adequate arcuate movement.

Figure 11:
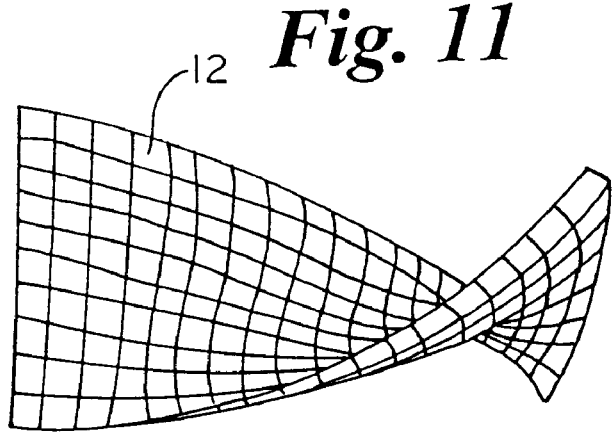
FIG. 11 shows the property of twistability of the fabric of the invention.
Figure 12A:
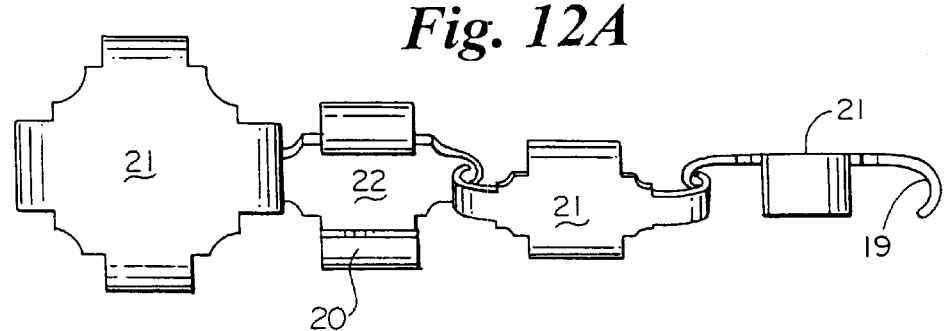
FIGS. 12A and B depict twistability of the invention showing actual platelets in a twisted condition.
Figure 12B:
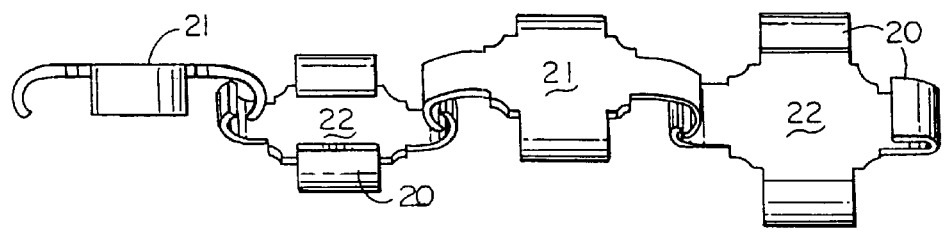

FIG. 11 shows a twisted fabric 11, where each block also represents a platelet 12. FIGS. 12A and B illustrate twisting of the fabric 11 as shown by actual depictions of the platelets 12.

Figure 25:
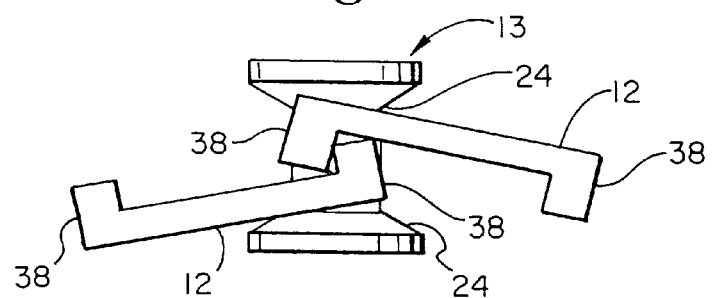
FIG. 25 shows the bending action facilitated by the truncated cone.

The hooks 16 by the nature of their construction and the mating engagement allow for movement of one platelet 12 with its top 21 up relative to each adjacent platelet 12 with its bottom 22 up. The mating engagement results in a loose coupling of the platelets 12. It is the loose coupling that allows the fabric 11 to approximate the flexibility characteristic of an elastomeric material. The hooks 16 allow for sliding movement of the platelets 12 relative to one another in a direction along a line in the plane of the platelet 12 and parallel to the tabs 15. To allow the platelets 12 to slidably move relative to one another in a direction away from each other, the reverse tab portion 20 is of a length that is less than the length of the arm 18 of the tab 15. The hooks 16 also allow movement in a downward and upward direction relative to the plane of the platelet 12, as shown in FIG. 25, which is a cross-section of a platelet 12 restrained by a rivet 13 as in the fabric of the present invention. FIG. 25 illustrates a platelet 12 with a planar hook 38, an alternative embodiment platelet 12. Movement in this direction is a function of the length of the rivet 13. The hook 16 also allows movement transverse to the tab 15. However, movement in the transverse direction is checked by the tab edge 25 contacting the rivet 13. The rivet 13 pin 23 in the compressed state of the fabric all but fills the aperture, thereby allowing virtually no transverse movement. Were it not for contact with the rivet 13 in both the compressed and the stretched configuration of the fabric 11, the mating hooks 16 would disengage and the fabric 11 would have the equivalent of a tear or a hole. However, there is a greater range of transverse movement of the platelets 12 relative to one another when the fabric 11 is stretched, because the area of the aperture 26 is greater in the stretched configuration then when compressed. This is illustrated by a comparison of FIGS. 7A, the compressed state, to 7B, the stretched state. And since the diameter of the pin 23 of the rivet 13 is a constant, the platelet 12 hooks 16 are allowed to move to fill the additional space in the aperture 26.

Figure 13A:
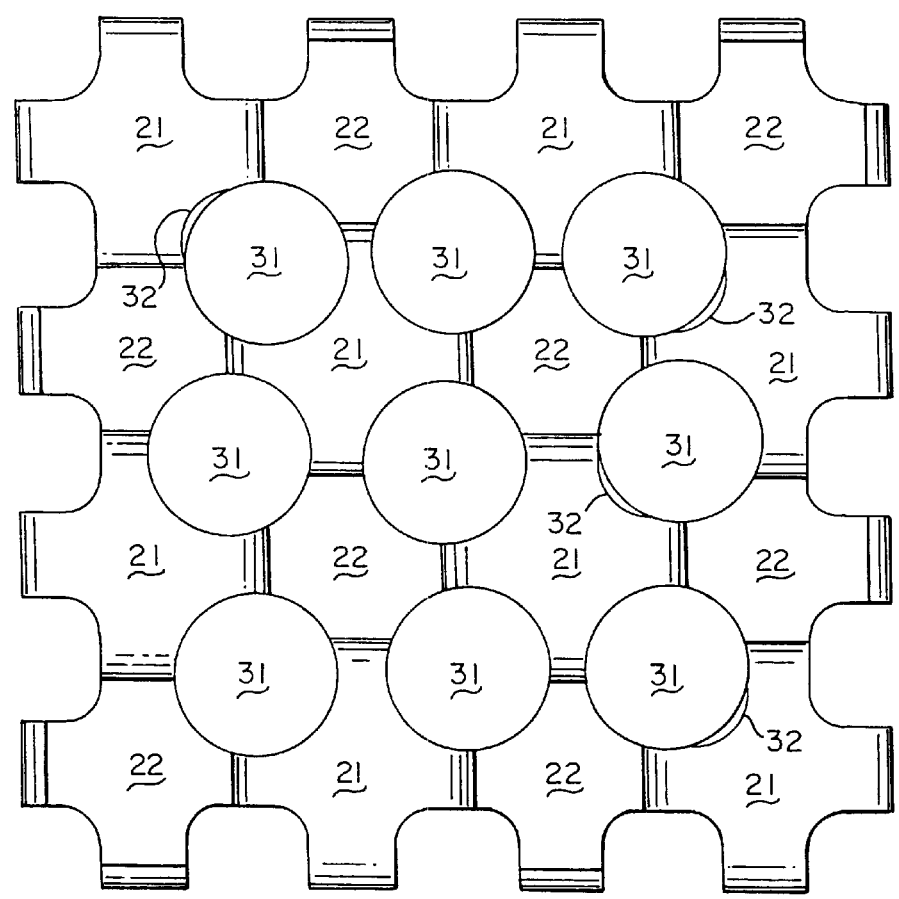
FIG. 13A depicts a fabric with the tops of the rivets too small to cover all of the apertures in a fully stretched configuration.

Were it not for the top 31 of the truncated cone 24, the space between the aperture 26 and the pin 23 would be large enough that a needle could penetrate the fabric 11. The top 31 of the truncated cone 24, shown in FIG. 3B, must, therefore, be of a diameter that is large enough that when the fabric 11 is fully stretched and pin 23 is in its worst case of having moved to the wall of the aperture 26, the top 31 covers the entire area of the aperture 26. In the best case when the fabric 11 is fully stretched, the pins 23 would all be positioned in the center of the aperture 26. In this case the diameter of the top 31 of the truncated cone 24 would only need to be slightly larger that the diameter of the aperture 26. However, this configuration never occurs. In practice the pins 23 assume a random distribution in the apertures 26. FIG. 13A illustrates a fabric 11 fully stretched. In FIG. 13A the tops 31 of four of the truncated cones 24 are of a diameter that is not large enough to completely cover spaces 32 between some of the rivets 13 and the apertures 26. The tops 31 of the other rivets 13 completely cover the apertures 26. After the fabric 11 is compressed and stretched again the new random distribution of the pins 23 in the apertures 26 will result in a new pattern of open spaces 32 between the apertures 26 and the pins 23. To correct the situation in FIG. 13A, the diameter of the tops must be increased. FIG. 13B illustrates different locations of the rivet 13 in the aperture 26 of a fully stretched fabric 11. The top 31 of the rivet 13 pin 23 has been made large enough that it always covers the aperture 26, regardless of where the pin 23 of the rivet 13 is located in the aperture 26. The size of the rivet 13 top 31 is constrained by the requirement that when the fabric is fully compressed, the tops 31 must not overlap each other. In turn the size of the aperture 26 when the fabric 11 is fully stretched depends upon the extent of stretchability of the fabric 11, which is a function of the length of the tab 15 arms 18. The diameter of the pin 23 of the rivet 13 also has an affect upon the size of the top 31 of the rivet 13 necessary to cover the aperture 26. The smaller the pin 23 cross-section, the larger the top 31 must be to cover the aperture 26.

Figure 15:
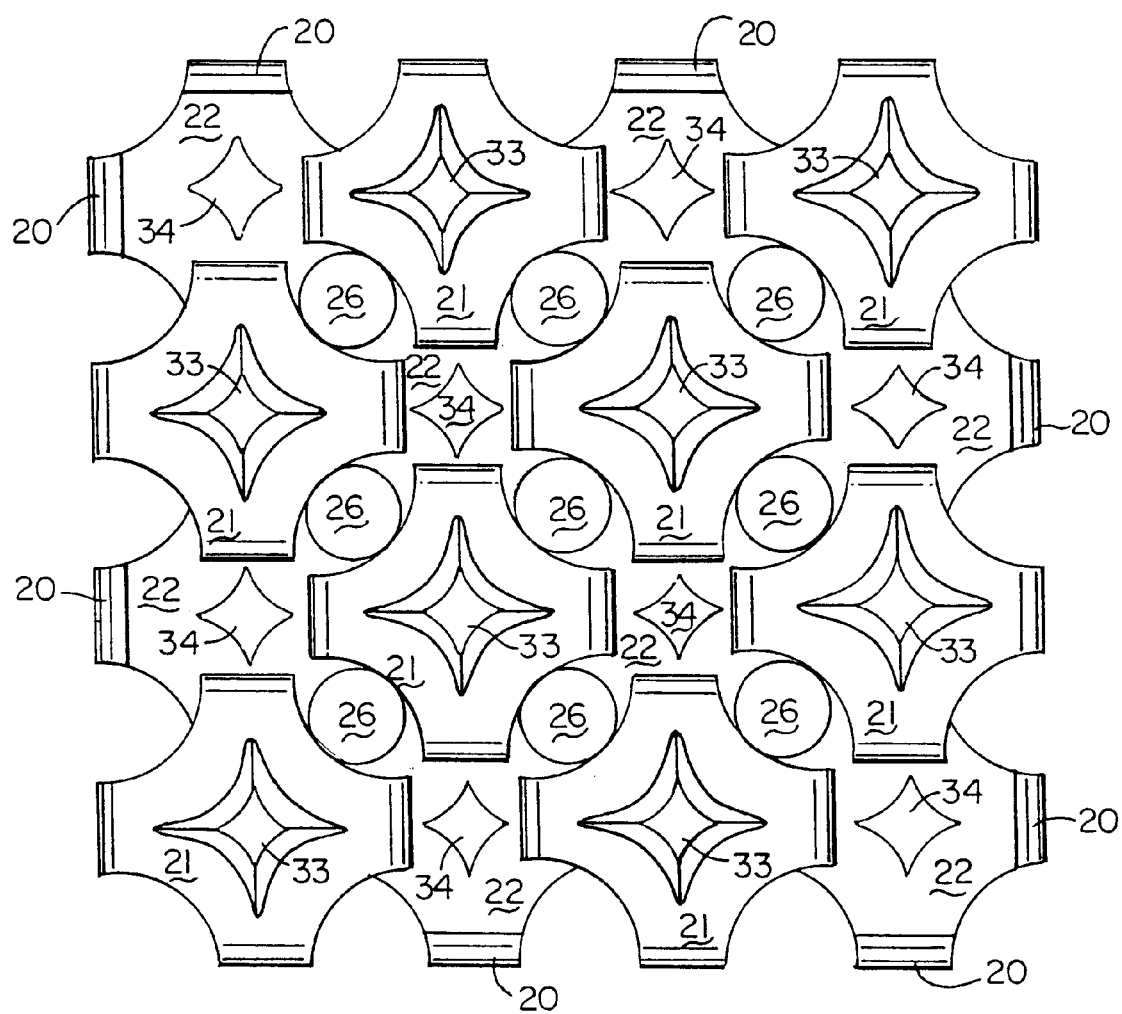
FIG. 15 illustrates the fabric of an alternative embodiment of the invention having heads and plugs with the rivets removed.
Figure 16:
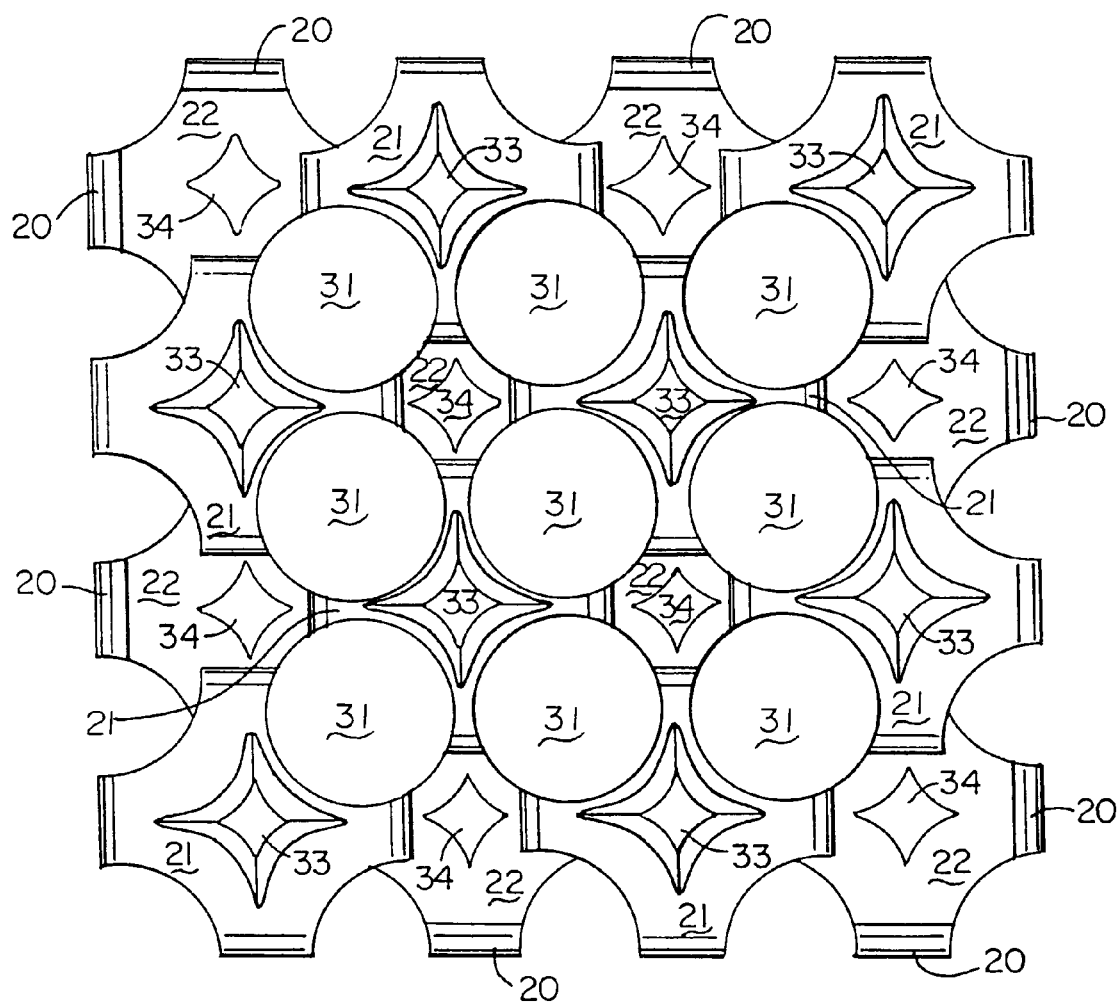
FIG. 16 illustrates the fabric of the alternative embodiment of the invention having heads and plugs with the rivets in place.

The fabric 11 assembled as shown in FIG. 1B in cross-section and in FIG. 1A in a perspective view from the top 21 of the platelet 12 presents an uneven surface, which for some applications may not be optimal. To alleviate the uneven surface, platelets 12, as shown in FIGS. 14, 15, and 16, have a head 33 extending upward from the top 21 of the base 14 portion of the platelet 12 and a plug 34 extending downward from the bottom 22 of the platelet 12. The head, shown in perspective in FIG. 14A is axially aligned with the center of the base 14. Its faces 40 are defined by intersecting cone shapes, which mate with the truncated cone 24 portion of the rivet 13. The top 43 surface of the head 33 is planer and in a plane parallel with the plane of the base 14 of the platelet 12. The height of the head 33 above the platelet 12 base 14 is the same as the height that the truncated cone 24 portion of the rivet 13 rises above the plane of the base 14 of the platelet 12. FIGS. 14B and C further illustrate the shape of the head 33.

The plug 34, shown in perspective in FIG. 14D, is axially aligned with the center of the bottom 22 of the base 14 of the platelet 12. Its faces 44 are defined by a radius equivalent to the radius of the top 31 of the truncated cone 24 for loose mating engagement with the top 31 of the truncated cone 24 when the fabric 11 is fully compressed. FIGS. 14C and F show the head 33 and the plug 34, respectively, affixed to the top 21 and the bottom 22 surface of the platelet 12 from the side.

FIGS. 15 and 16 depict the alternate embodiment of the fabric 11 with the heads 33 and the plugs 34. FIG. 15 has the truncated cones 24 of the rivets 13 removed to better illustrate the spatial relationship of the rivets 13, heads 33, and the plugs 34. FIG. 16 shows the rivets 13 with the top 31 of the truncated cones 24 in place. This figure shows how the tops 31 of the truncated cones 24 loosely mate with the heads 33 and with the plugs 34 to allow movement relative to one another, for example rotational movement of the rivets, and also close packing density when the fabric 11 is at its fully compressed position as it is shown in FIGS. 15 and 16. As illustrated in FIG. 16, the flat top surfaces of the heads 33, which rise to the same level as the tops 31 of the truncated cones 24 gives a more overall even surface to the fabric 11. There remains some texture to the fabric 11 since the heads 33 and the plugs 34 do not completely infill the fabric 11, especially when the fabric 11 is fully stretched. However, the depressed surface area is largely relieved, which satisfies even the most demanding applications.

The invention has been described with a square shaped platelet 12 having tabs 15 extending from its base 14. This shape is the preferred embodiment, but the fabric of the invention is of utilitarian value when the platelets 12 are constructed of different shapes. For example, an equal sided triangular shape is also efficacious in that the resulting fabric possesses the desired three axis of flexibility and also with the use of a modified rivet presents a fabric without gaps which stops a needle from penetrating the fabric 11.

Another embodiment of the invention is illustrated in FIGS. 17 through 23. FIG. 17A depicts a fabric 11 constructed from a modified platelet 12 and a modified rivet 13. The modified platelet 12 has bevels 35 at the distal end of the each tab 15 where the tab edge 25 and the distal end of the tab 15 meet. The edges 25 of adjacent tabs 15 of the same platelet 12 are connected by a straight edge 36 having as a point in the straight edge 36 the intersection of the edges 17 of the base 14 of the platelet 12( shown in dotted lines in FIG. 17A) and terminating at the intersection of the straight edge 36 and the edge 25 of one tab 15 and on the other end of the straight edge 36 at the intersection with the edge 25 of the adjacent tab 15 so that the edges 25 of the tabs 15 in which the straight edge 36 terminates are both of the same length.

Figure 17A:
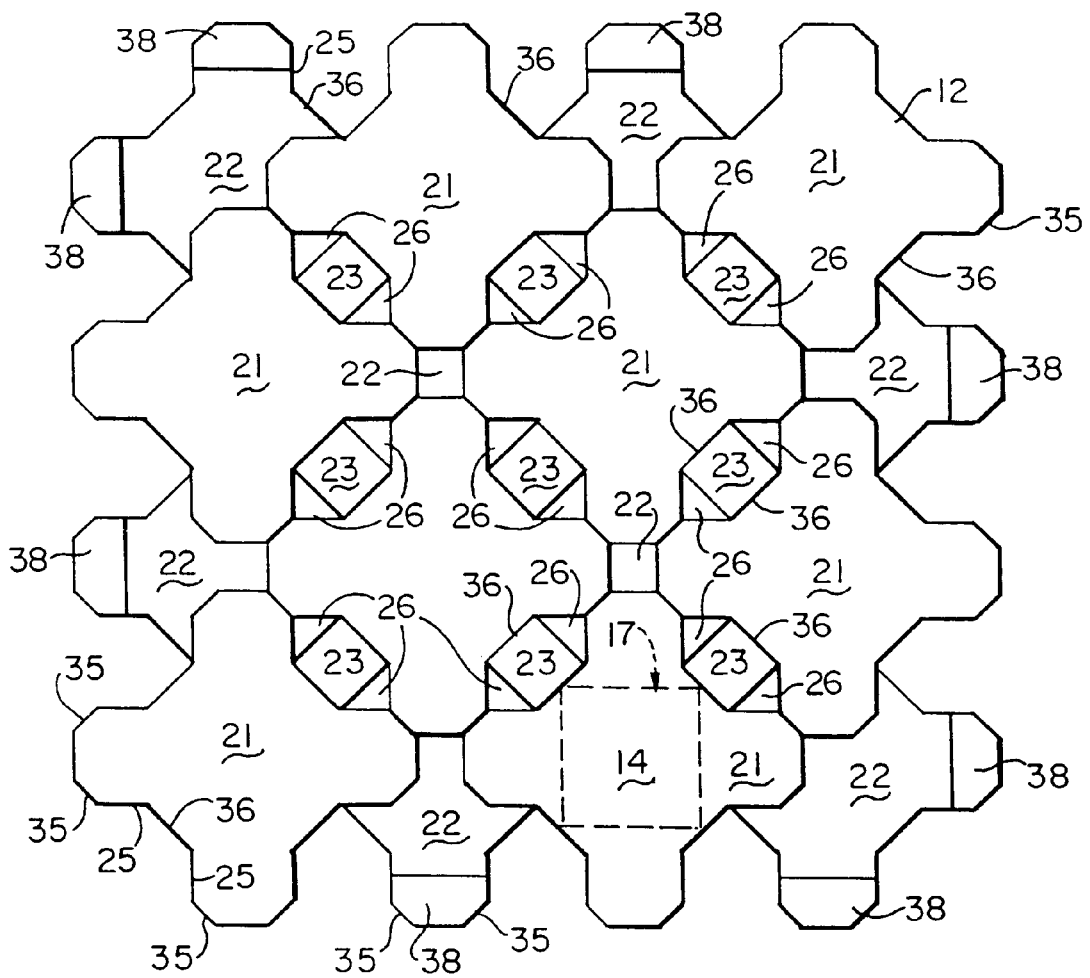
FIG. 17A is a further alternative embodiment of the fabric in the most compressed configuration having beveled edges on the tab distal ends and between tabs, shown without rivets.
Figure 17B:
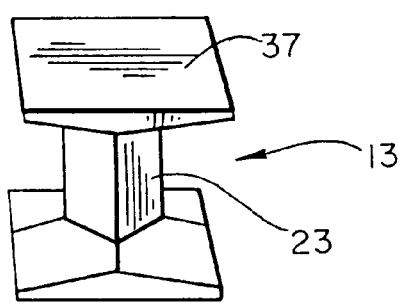
FIG. 17B is a perspective view of the rivet to be used with the embodiment shown in FIG. 17A.

The pin 23 of the rivet 13 instead of being round is square. Each side of the square pin 23 is the same length as the straight edge 36 of the platelet 12. This embodiment allows for an even closer packing of the platelets 12 than the design using round pins 23. In this embodiment, the platelets 12 and the pins 23 nest closer together as shown in FIG. 17 when in the fully compressed configuration. FIG. 17B illustrates the square pin 23 and square plate rivet head 37 of this embodiment.

Figure 18:
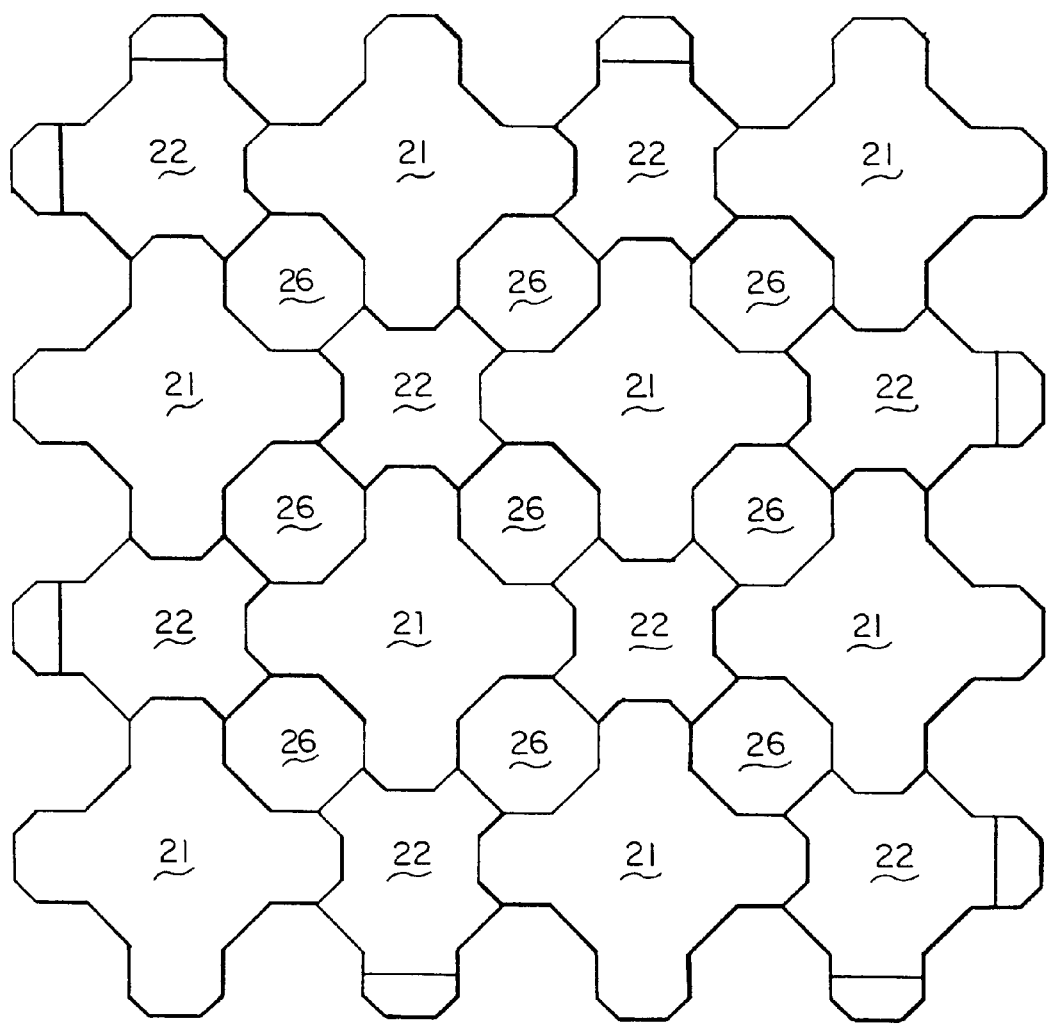
FIG. 18 illustrates the alternative embodiment fabric of FIG. 17 in its most stretched configuration without rivets.
Figure 19:
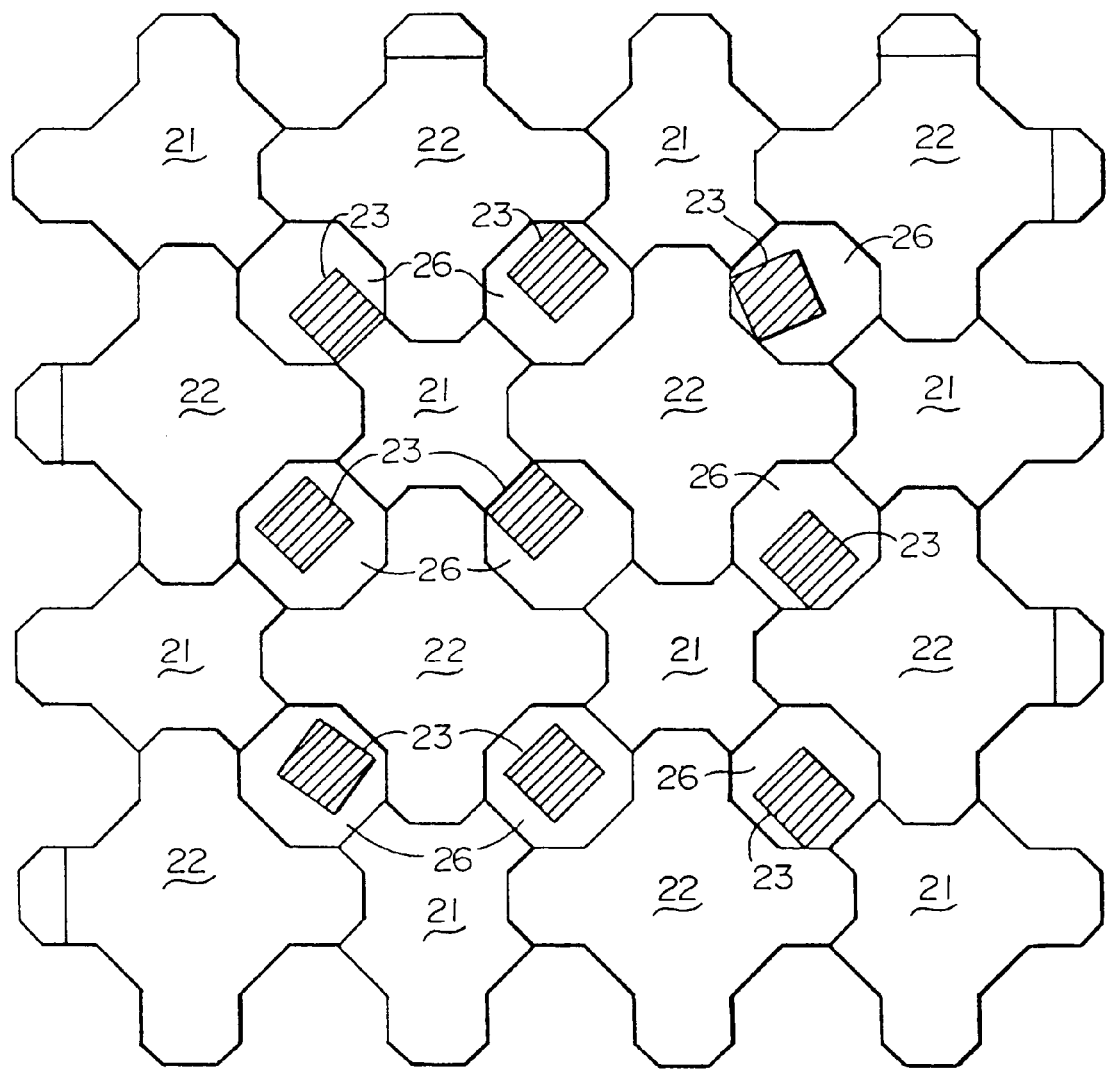
FIG. 19 is the same as FIG. 18 except that square pin portions of alternative embodiment rivets are inserted.
Figure 20:
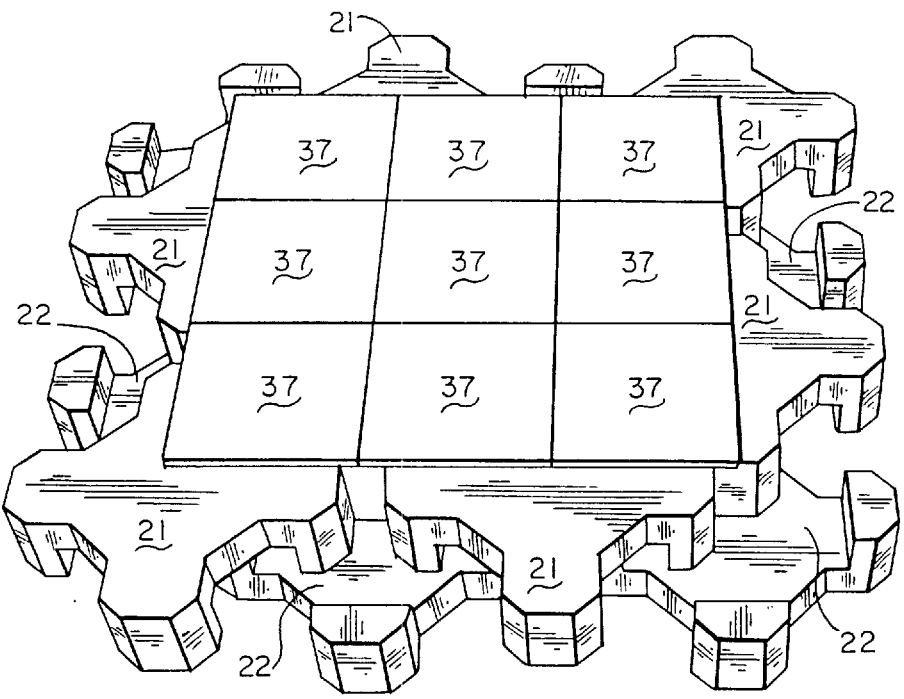
FIG. 20 shows the square plate rivet heads of the alternative embodiment rivet in the fabric shown in FIG. 17 in its compressed state.
Figure 21:
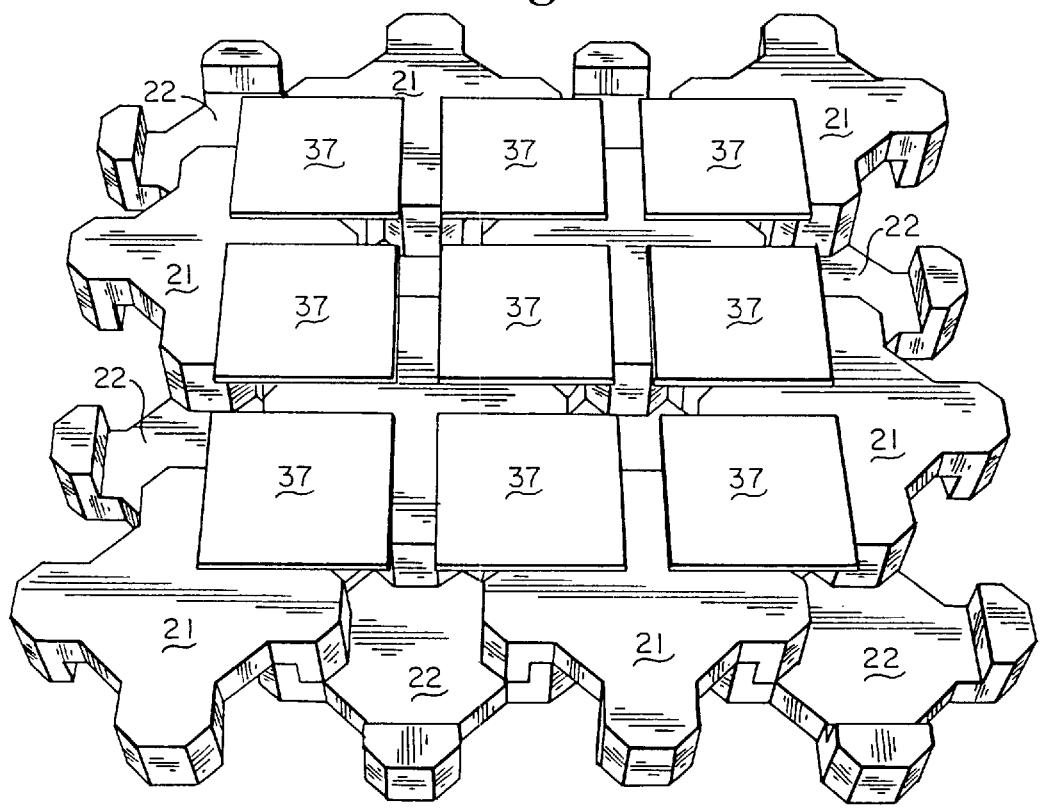
FIG. 21 depicts the fabric of FIG. 20 in a fully stretched state with the square plate rivet heads.
Figure 22:
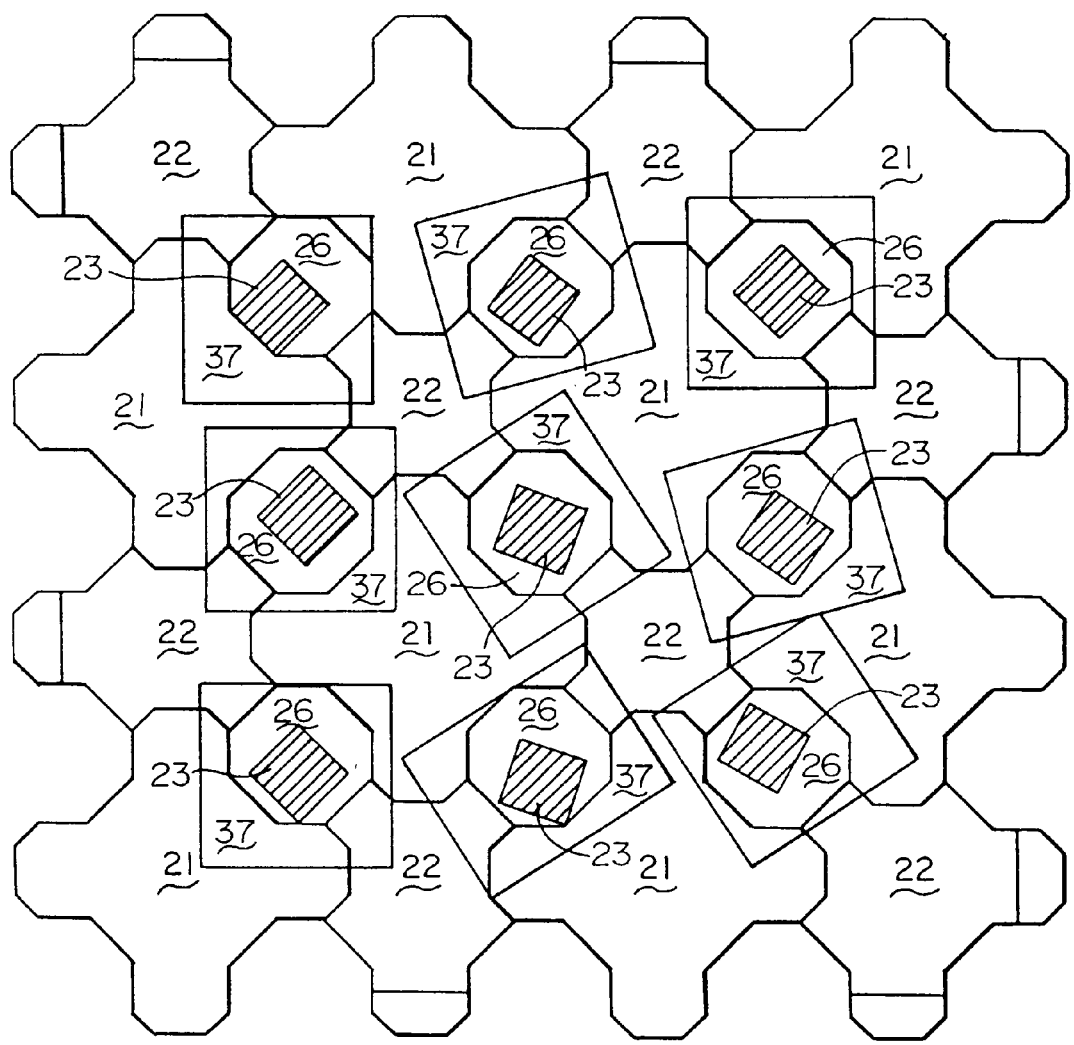
FIG. 22 shows a portion of the fabric of the alternative embodiment with the rivets in place in differing locations with the square plate rivet heads fully covering the apertures.
Figure 23A:
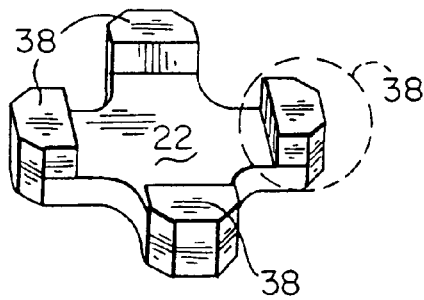
FIG. 23 depicts an alternative embodiment platelet with a planar hook.
Figure 23B:
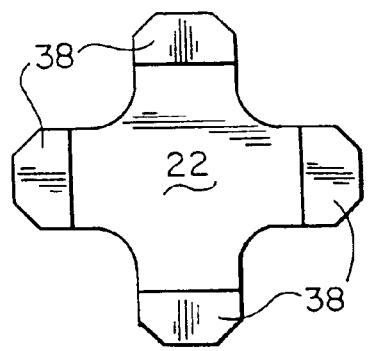
Figure 23C:
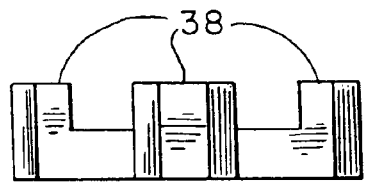
Figure 23D:
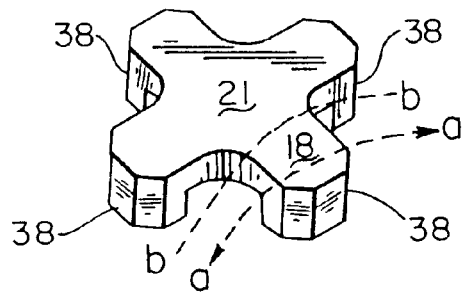
Figure 23E:
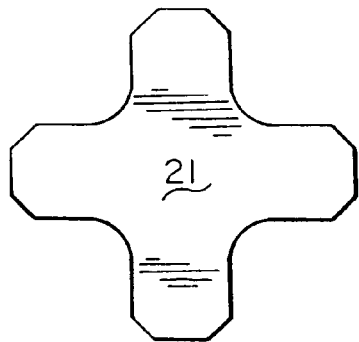
Figure 23F:
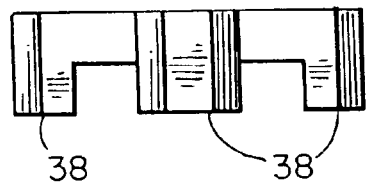

FIG. 18 illustrates the fabric 11 of this embodiment in its fully stretched configuration without the pins 23 inserted. Without the pins 23 inserted it can clearly be seen that the aperture 26 is hexagonal in shape. FIG. 19 shows the fabric 11 of this embodiment in its fully stretched configuration with the pins 23, illustrating that the pins 23 of the rivets 13 are loosely fitted into the aperture 26 made by the surrounding adjacent platelets 12. FIG. 20 shows the fabric 11 in its fully compressed configuration. The rivet 13 instead of terminating in a truncated cone 24, terminates in a square plate rivet head 37. When the fabric 11 is fully compressed, the rivets 13 are forced into the rectilinear configuration shown in FIG. 20. This configuration promotes stretchability by allowing for the large surface area of the square plate rivet head 37, which provides maximum coverage of the large aperture 26 formed when the fabric 11 is stretched to the maximum and yet does not retard compression of the fabric 11 because it nests compactly in the rectilinear shape. FIG. 21 shows the fabric 11 in the stretched mode and illustrates the complete coverage of all of the apertures 26, providing a continuous closed web of fabric 11 which will resist penetration by a needle or a suture. FIG. 22 shows a portion of the fabric 11 of FIG. 21 with the square plate rivet head 37 of the rivet 13 and the square pin 23. The rivet 13 the pin 23 in the upper left hand position of FIG. 22 has moved adjacent to the side of the aperture 26 while the other rivets 13 have moved to other random positions. Even in these randomly diverse positions, the square plate rivet heads 37 cover the apertures 26. The square plate rivet heads 37 cover the apertures 26 even though they are not oriented in a rectilinear configuration, but in a random configuration.

Figure 24A:
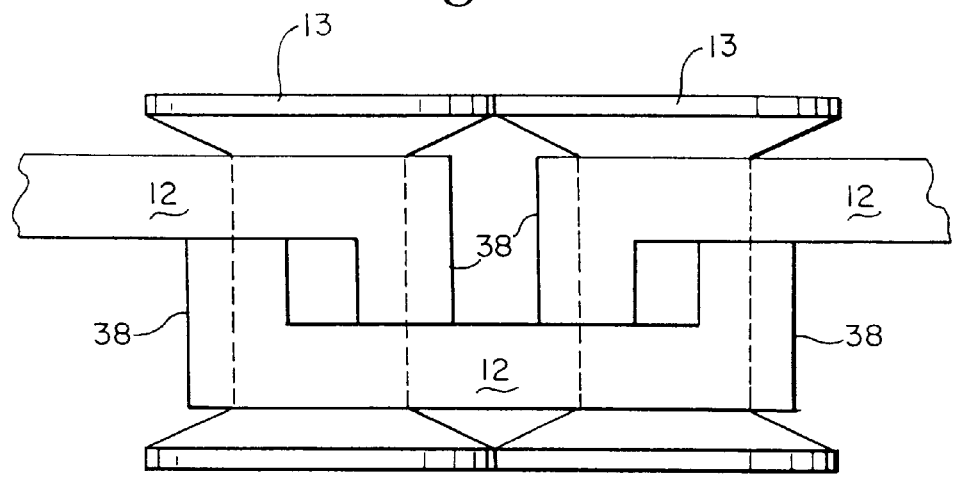
FIGS. 24A and 24B shows a cut away elevation view of the invention using the platelet with the planar hook in the compressed and stretched configurations, respectively.
Figure 24B:
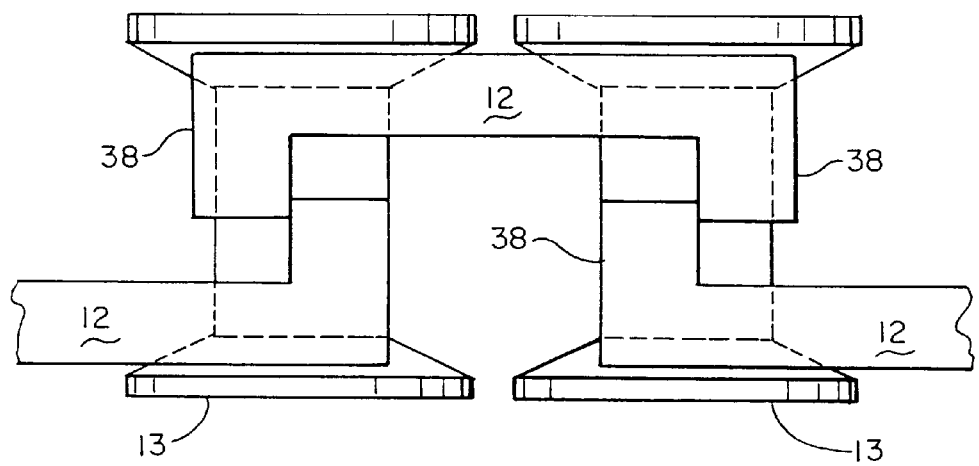

An alternative to the platelet 12 shown in FIG. 2 is depicted in FIG. 23. The arm 18 of the tab 15, which lies between dotted lines a—a and b—b in FIG. 23D, terminates in planar hook 38, shown in the dotted circle 38 in FIG. 23A, depending downward from the plane of the arm 18 and the base of the platelet 12 at a right angle to the plane of the arm 18. FIG. 23A shows the alternative embodiment in a perspective view form the bottom side. The planar hook 38 is shown with a thickness greater than the thickness of the base 14 of the platelet 12. This additional wall thickness may be added for some very demanding applications where tear strength parallel to the plane of the fabric must be high. Additional wall thickness may increase the cost of manufacturing somewhat. For most applications a wall thickness the same as the base 14 of the platelet 12 is adequate. FIG. 23D shows the platelet 12 from the top. FIGS. 23B through F are plan and elevation views of the alternative embodiment of the platelet. This alternative embodiment platelet 12 configuration lends itself to somewhat lower manufacturing and assembly costs. FIG. 24A shows the alternative embodiment in a cut-away cross section with rivets 13 in a fully compressed state. FIG. 24B illustrates the fully stretched state.

FIG. 25 depicts how the truncated cone 24 facilitates bending of the fabric 11 with the alternative embodiment platelet 12 having the planar book 38. The truncated cone 24 also facilitates bending with the platelet 12 with the hook 16 with the reverse tab 20.

Figure 26B:
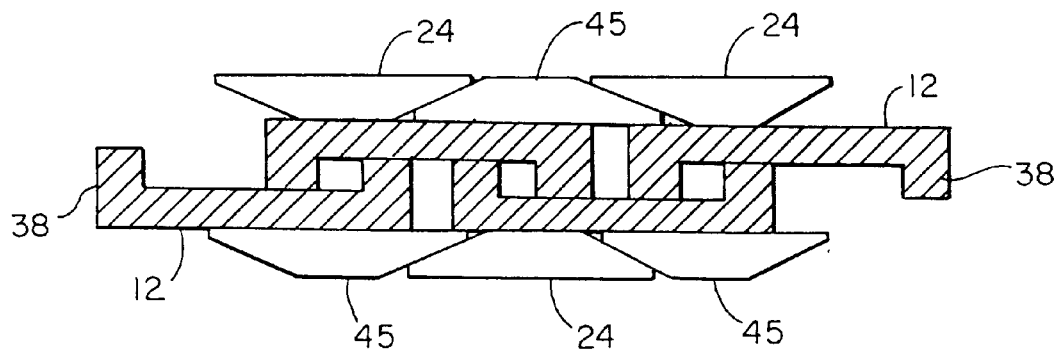
FIGS. 26A and 26B shows elevational views of an alternative embodiment of the fabric incorporating alternate rivets having inverted truncated cones.
Figure 26A:
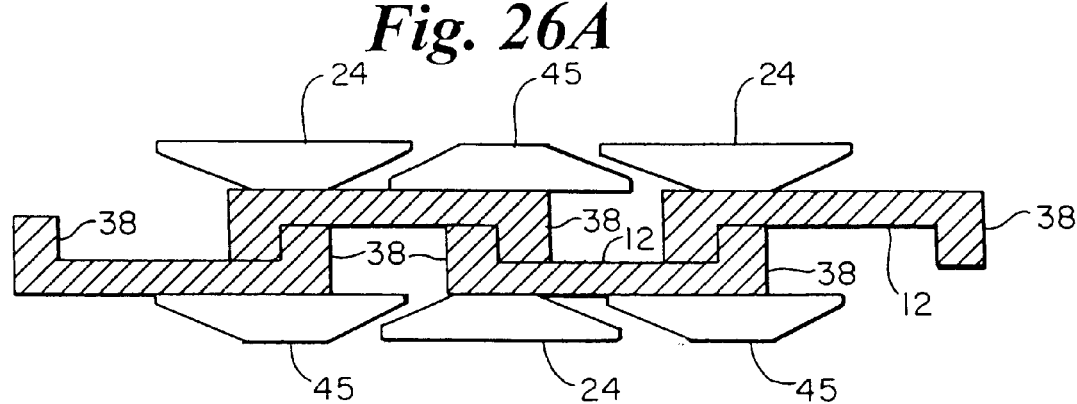
Figure 27A:
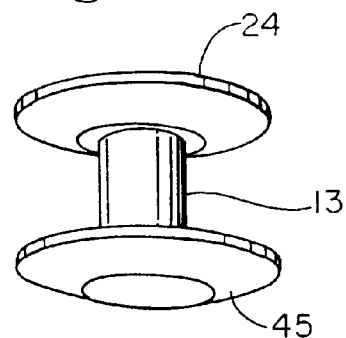
FIG. 27A shows a perspective views of the rivet shown in FIGS. 26A and 26B.
Figure 27B:
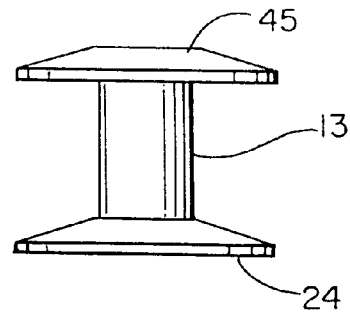
FIG. 27B is an elevational view of the rivet.

FIGS. 26A and B show yet another alternative embodiment fabric 11. In this embodiment, alternate rivets 13 have their truncated cones 24 inverted. When the fabric 11 is stretched, as shown in 26A, the platelets 12 pull apart until they are restrained by the overlapping planar hook 38. If the fabric 11 must bend, the truncated cones 24 and the inverted truncated cones 45 slide upward over each other to allow the bending. When the fabric 11 is compressed, as shown in FIG. 26B, the truncated cones 24 and inverted truncated cones 45 fully nest together. The truncated cones 24 and inverted truncated cones 45, as shown in FIGS. 26A and B, present a solid surface to a puncturing instrument in either the fully compressed state or the fully stretched state. When the fabric 11 is extended, FIG. 26A, the diameter of the truncated cones 24 and inverted truncated cones 45 is large enough that there is overlap to stop the penetration of a sharp instrument. FIG. 27A is a perspective view and FIG. 27B is an elevational view of a rivet 13 with one of its truncated cones 24 inverted.

Figure 28A:
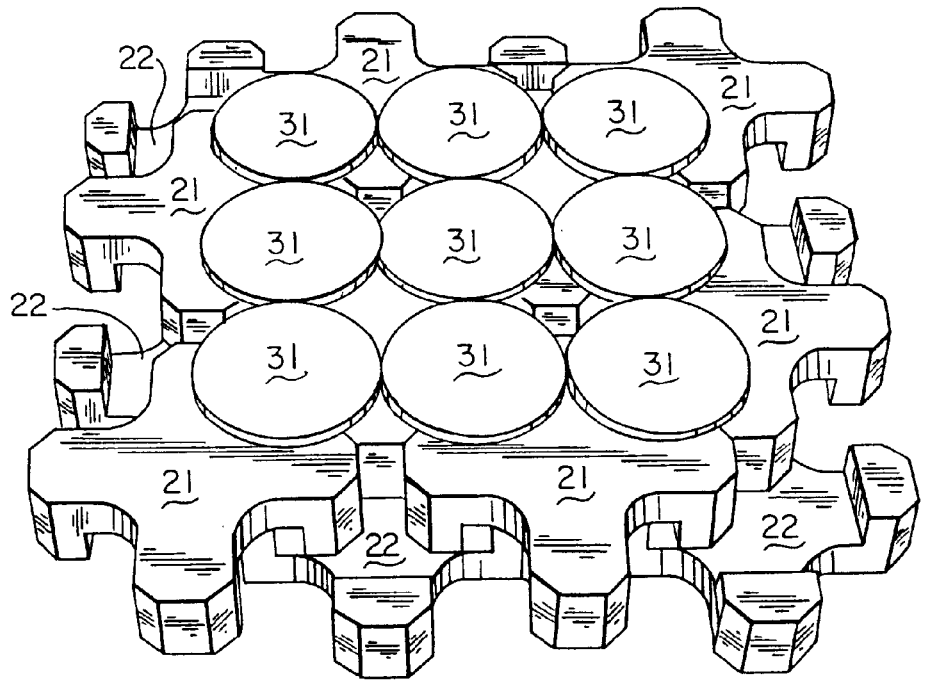
FIG. 28A illustrates a further embodiment of the fabric with platelets having a rounded edge between tabs and beveled distal tab ends in a compressed configuration.
Figure 28B:
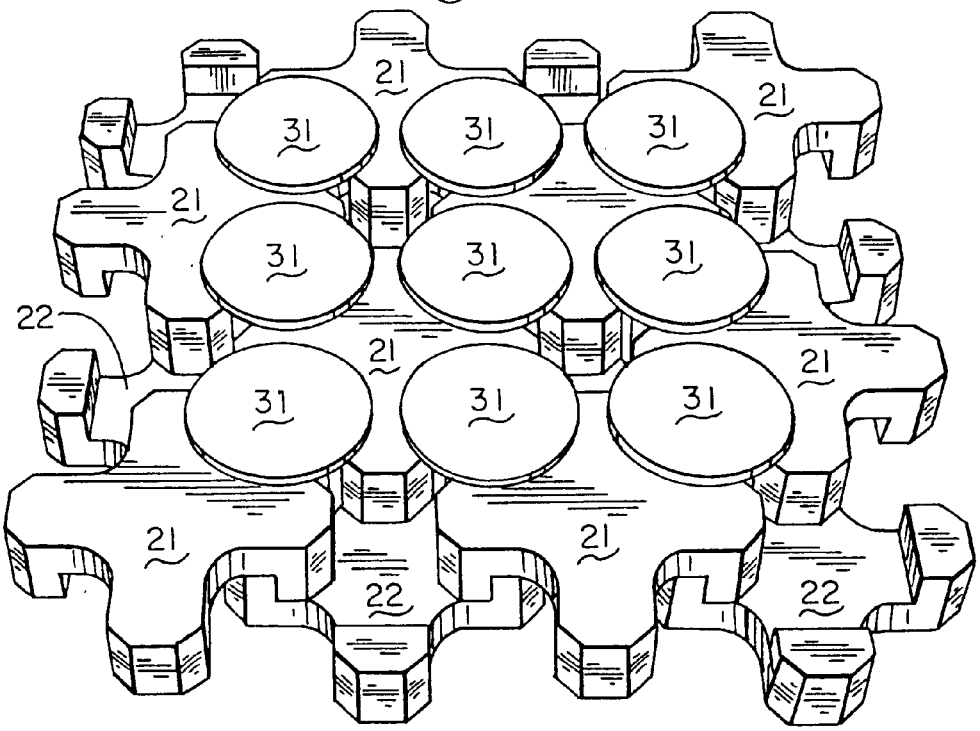
FIG. 28B illustrates the fabric of 28A in a stretched configuration.

FIGS. 28A and 28B illustrate a further embodiment of the fabric 11 with platelets 12 having a rounded edge 25 between tabs 15 and tab bevels 35 on the distal end of the tabs 15 in a compressed and a stretched configuration, respectively.

While this specification illustrates and describes embodiments of the invention, it is understood that this invention is capable of modification and therefore the invention is not limited to the precise details set forth in this specification. This invention includes such changes and alterations as fall within the purview of the following claims.

What is claimed as the invention is:

1. A fabric comprised of a plurality of platelets arranged in a sheet, each platelet having a tab depending from each edge of each platelet so that the tabs of each adjacent platelet slidably interconnect.

2. A garment protective against punctures and cuts incorporating the puncture and cut resistant fabric of claim 1.

3. A fabric comprised of:
   a. a plurality of platelets arranged in a sheet, each platelet having a tab depending from each edge of each platelet so that the tabs of each adjacent platelet slidably interconnect, and an aperture formed at interconnected tabs of adjacent platelets; and
   b. a rivet inserted into each aperture, to form a flexible array having its entire surface area covered by platelets and rivets.

4. The fabric of claim 3, wherein the base of the platelet is planar.

5. The fabric of claim 4, wherein the tab extends from the edge of the platelet in the same plane as the base of the platelet.

6. The fabric of claim 5, wherein the distal end of an arm of the tab terminates in an arc extending away from the plane of the base of the platelet.

7. The fabric of claim 6, wherein the arm of the tab depends from the top of the base of the platelet and is aligned with the tab.

8. The fabric of claim 1, wherein the arc in which the tab terminates forms a hook.

9. The fabric of claim 6, wherein the distal end of the arm of the tab terminates in a planar hook.

10. The fabric of claim 9, wherein the planar hook depends from the top of the base of the platelet and is aligned with the tab.

11. The fabric of claim 4, wherein the platelets are arranged in an array wherein each platelet having its top upward is connected to adjacent platelets having its bottom upward.

12. The fabric of claim 11, wherein the tabs of each adjacent platelet are interconnected by mating the opposing hooks of the adjacent platelets.

13. The fabric of claim 12, wherein the reverse tab portion is of a length that when the fabric is fully compressed, the reverse tab portions of adjacent platelets overlap, whereby the platelets are restrained from moving at an angle to its planar base to a degree that the platelets become uncoupled.

14. The fabric of claim 12, wherein the portion of the hook which reverses back towards the edge of the base of the platelet is of a length that is less than the length of the arm of the tab, whereby the platelets are free to slidably move relative to one another in a direction away from each other.

15. The fabric of claim 12 wherein the radius of the hooks is large enough to allow the hooks of two adjacent platelets to move in an arc relative to each other.

16. The fabric of claim 15, wherein the edges of the tab are free of faces depending therefrom at an angle to the plane of the platelet base, whereby the platelets are free to slidably move transversely relative to one another.

17. The fabric of claim 11, wherein the platelets and the rivets are all identical.

18. The fabric of claim 4, wherein the top of the base of the platelet has a head axially aligned with the center of the base of the platelet.

19. The fabric of claim 18, wherein the head is shaped in the form of a pyramid with its top truncated, each face of the head defined by an inverted truncated cone for mating engagement with the truncated cones of adjacent rivets.

20. The fabric of claim 18, wherein the bottom of the base of the platelet has a plug axially aligned with the center of the base of the platelet.

21. The fabric of claim 20, wherein the plug is shaped in the form of a pyramid with its top truncated, each face of the plug defined by an inverted truncated cone for mating engagement with the truncated cones of adjacent rivets.

22. The fabric of claim 3, wherein the width of the tab is less than the length of the edge of the base of the platelet.

23. The fabric of claim 3, wherein the base of the platelet is a polygon having equal sides.

24. The fabric of claim 23, wherein the base of the platelet is a polygon having four equal sides.

25. The fabric of claim 22, wherein the intersection of adjacent edges of the base of the platelet is a concave arc.

26. The fabric of claim 3, wherein a plurality of rivets are inserted perpendicular to the plane of the fabric through each of the apertures formed by the opposing edges of the interconnected tabs and the edges of the platelets to form a flexible array having its entire surface area covered by platelets and rivets.

27. The fabric of claim 26, wherein each rivet comprises a pin with truncated cone heads affixed to each end of the pin, whereby the pins are locked into the fabric array.

28. The fabric of claim 27, wherein the cross-section of the pins is less than the cross-section of the aperture when the fabric is fully compressed, whereby the rivets are moveable at right angles to the plane of the fabric.

29. The fabric of claim 27, wherein the surface of the truncated cone ends of the rivet distal from the pin cover the aperture when the fabric is fully stretched regardless of the location of the pin in the aperture.

30. The fabric of claim 26, wherein each rivet comprises a pin with square plate heads affixed to each end of the pin.

31. The fabric of claim 26, wherein each rivet comprises a pin with a truncated cone head at one end and an inverted truncated cone head at the other end.

32. The fabric of claim 26, wherein the pin of the rivet is round.

33. The fabric of claim 26, wherein the pin of the rivet is square.

34. The fabric of claim 3, wherein the fabric is sandwiched between upper and lower layers of material.

35. The fabric of claim 34, wherein the material of at least one of the layers is an elastomeric polymer.

36. The fabric of claim 34, wherein the elastomeric encased fabric is formed into medical apparel.

37. The fabric of claim 3, wherein the platelet is formed of a thin walled sheet of material from the group consisting of a metal, metal alloy, plastic, and ceramic.

38. The fabric of claim 37, wherein the platelet is formed of a thin walled sheet from the group consisting of a metal, metal alloy, plastic, and ceramic having a thickness sufficient to resist a specified piercing or cutting force.

39. The fabric of claim 3, wherein the rivet is formed of material from the group consisting of a metal, metal alloy, plastic, and ceramic.

40. The fabric of claim 3, wherein the intersection of adjacent edges of the base of the platelet is a straight edge between the tabs.

41. A method of fabricating a puncture and cut resistant composite glove comprising the steps of:
   a. forming an inner glove of a fluid barrier material;
   b. placing a fabric over the inner glove, the fabric comprising (i) a plurality of identical polygonal platelets having equal sides, (ii) each platelet having a tab depending from each edge of each platelet in the same plane as the main body of the platelet with the end of the tab distal from the base of the platelet terminating in a hook extending away from the plane of the platelet base, (iii) the identical platelets arranged in an array with the top of every other platelet in both rows and columns rotated so that the bottom of the platelet is up, (iv) the hooks of the tabs of each adjacent platelet interconnected, (v) with rivets inserted, perpendicular to the fabric through the apertures formed by the edges of the interconnected tabs, and (vi) each rivet capped at its end, the surface of the cap of a size that will cover the aperture when the fabric is fully stretched regardless of the location of the pin in the aperture; and
   c. placing an outer glove over the fabric.

42. The method of claim 41 further comprising the step of affixing the fabric at selected points to the inner and outer glove.

43. The method of claim 41, further comprising the step of applying a lubricant to the fabric.

44. A sheet comprised of a plurality of interconnected platelets, wherein each platelet has a tab depending from each edge of each platelet, so that the tabs of each adjacent platelet slidably interconnect, and an aperture formed at interconnected tabs of adjacent platelets.

45. The sheet of claim 44, also comprising a means for interlocking the interconnected platelets.

46. The sheet of claim 45, wherein the means for interlocking the interconnected platelets is loosely interlocking.

47. The sheet of claim 46, wherein the means for interlocking the interconnected platelets is a rivet through each aperture in the sheet.

48. The sheet of claim 47, wherein the rivet is comprised of a pin and a truncated cone at each end of the pin.

49. The sheet of claim 48, wherein a cross-sectional area of the pin of the rivet is less than or equal to a cross-sectional area of the aperture when the sheet is fully compressed so that when the sheet is stretched, the platelets are rotatable relative to one another in a plane of the sheet and in a direction at an angle to the plane of the sheet.

50. The sheet of claim 48, wherein a cross section of the end of the truncated cone of the rivet distal from the pin is larger than a cross section of the aperture when the sheet is fully stretched and the pin is located at any point adjacent to the periphery of the aperture.

51. The sheet of claim 48, wherein a length of the rivet is predetermined to restrict a distance of movement of the platelets in a direction substantially perpendicular to the plane of the sheet to maintain overlap of the planer hooks of adjacent platelets.

52. A method of protecting a surface from punctures and cuts comprising the steps of:
   a) forming a fabric comprised of an array of interconnected platelets,
      wherein each platelet has an integral means for slidable interconnection with adjacent platelets; and
   b) covering the surface to be protected with the fabric.

53. A cut and puncture resistant material fabric which is also a barrier to transmission of fluids comprising a two dimensional sheet of platelets having tabs on each edge of the base of the platelet for loose interconnection of the platelets, combined with an elastomeric layer.

* * * * *